United States Patent [19]
Welsh et al.

[11] Patent Number: 5,939,393
[45] Date of Patent: Aug. 17, 1999

[54] BACTERICIDAL FACTOR IN HUMAN AIRWAY SURFACE FLUID AND USES THEREOF

[75] Inventors: Michael J. Welsh, Riverside; Jeffrey J. Smith, Iowa City; Sue M. Travis, Iowa City; Everett P. Greenberg, Iowa City, all of Iowa

[73] Assignee: University Of Iowa Research Foundation, Iowa City, Iowa

[21] Appl. No.: 08/840,876

[22] Filed: Apr. 17, 1997

Related U.S. Application Data

[60] Provisional application No. 60/041,601, Mar. 25, 1997.
[51] Int. Cl.$^6$ .......................... A61K 38/00; A61K 38/02; A01N 37/18
[52] U.S. Cl. ........................... 514/21; 530/300; 530/324; 514/2
[58] Field of Search .................................. 530/324, 300; 514/21; 424/520

[56] References Cited

U.S. PATENT DOCUMENTS

| | | | |
|---|---|---|---|
| 5,202,420 | 4/1993 | Zasloff et al. | 530/324 |
| 5,432,270 | 7/1995 | Zasloff et al. | 536/23.5 |

OTHER PUBLICATIONS

Ellison et al. (1984) Clinical Research, 32(2), "Isolation of an Antibacterial Peptide from Human–Lung Lavage", p. A367.

Ellison et al. (1985) J. Infect. Dis., 151(6), "Isolation of an Antibacterial Peptide from Human Lung Lavage Fluid", pp. 1123–1129.

Diamond et al. (1991) Proc. Nat. Acad. Sci. USA, 88(9), "Tracheal Antimicrobial Peptide, A Crysteine–Rich Peptide from Mammalian Tracheal Mucosa: Peptide Isolation and Cloning of cDNA", pp. 3952–3956.

Diamond et al. (1993) Proc. Nat. Acad. Sci. USA, 90, "Airway Epithelial Cells are the site of Expression of a Mammalian Antimicrobial Peptide Gene", pp. 4596–4600.

Lehrer et al. (1993) Annu. Rev. Immunol., 11, "Defensins: Antimicrobial and Cytotoxic Peptides of Mammalian Cells", pp. 105–128.

Martin et al. (1995) J. Leukocyte Biol., 58(2), "Defensins and Other Endogenous Antibiotics of Vertabrates", pp. 128–136.

Smith et al. (1996) Cell, 85(2), "Cystic Fibrosis Airway Epithelia Fail to Kill Bacteria Because of Abnormal Airway Surface Fluid", pp. 229–236.

*Primary Examiner*—Jon P. Weber
*Attorney, Agent, or Firm*—Zarley, McKee, Thomte, Voorhees & Sease

[57] ABSTRACT

A bactericidal factor isolated from the surface fluid of airway epithelial cells and uses therefore is described. The bactericidal factor is characterized as having the following features: a) a molecular weight of less than 10 kd; b) heat stable; c) broad spectrum activity including gram positive and gram negative bacteria, fungi, and methicillin resistant Staphylococcus; and d) decreased antimicrobial activity in increasing salt concentration.

3 Claims, 19 Drawing Sheets

▲ Apical
○ Basolateral

☐ PAO1S
■ Clinical isolate

—○— Clearing Units
—●— LU Activity (Units)

BACTERICIDAL FACTOR IN HUMAN AIRWAY SURFACE FLUID AND USES THEREOF

CROSS-REFERENCE TO RELATED APPLICATIONS

This application claims the benefit of U.S. Provisional application Ser. No. 60/041,601 filed on Mar. 25, 1997, which was converted from U.S. application Ser. No. 08/634,633 filed Apr. 18, 1996, now abandoned.

BACKGROUND OF THE INVENTION

Cystic fibrosis is a human genetic disease of epithelia. Although the survival rate of those suffering with cystic fibrosis has improved in recent years, the median age for patient survival is still only about twenty five to thirty years despite intensive supportive and prophylactic treatment. Today cystic fibrosis remains the most common congenital disease among Caucasians, where it has a prevalence of about one in two thousand live births, and is uniformly fatal. Nearly all patients suffering from the disease develop chronic progressive disease of the respiratory system, the most common cause of death being pulmonary disease. Also, in the majority of cases, pancreatic dysfunction occurs; hepatobiliary and genitourinary diseases are also frequent. Because of the multi-system clinical manifestations of the disease, current methods of treatment for the disease have focused on therapeutic approaches to reduce the symptoms of cystic fibrosis.

For example, U.S. Pat. No. 5,100,647 to Agus, et al, discloses a method for treating cystic fibrosis by administration of the compound sparteine (dodecahydro-7, 14methano-2H, 6H-di-pyrido [1,2-a: 1',2'-e] [1,5] diazocine), acting as a direct exogenous activator of chloride conductants in epithelial airways. U.S. Pat. No. 5,179,001 to Young, et al, discloses a method of treating pulmonary complications associated with cystic fibrosis caused by the gram negative bacterium *Pseudomonas aeruginosa.* U.S. Pat. No. 4,826,679 to Roy relates to an oral composition for alleviating digestive manifestation in persons afflicted with cystic fibrosis comprising a therapeutic amount of taurine.

Despite much advancement in the treatment of the symptoms of cystic fibrosis very little has been accomplished to effectively "cure" the disease at a molecular level.

One method of gene therapy proposed is U.S. Pat. No. 5,149,797 disclosing a method of site specific alteration of RNA and production of encoded polypeptides. This invention is drawn to correcting the abnormal mRNA present in individual cells, cleaving the mRNA by site directed RNAase followed by introduction of the appropriate oligoribonucleotide followed by endogenous RNA ligase and thus production of a wild-type mRNA encoding a normal protein product which then may be translated to produce the correct protein.

The past few years have brought dramatic advances in our knowledge of the molecular and cellular basis of CF (for reviews see: Collins, F. S., (1992), "Cystic Fibrosis: Molecular Biology and Therapeutic Implications", *Science* 256, 774–779; Riordan, J. R., (1993), "The Cystic Fibrosis Transmembrane Conductance Regulator", *Annu. Rev. Physiol.* 55, 609–630; Welsh, M. J., (1995), "Cystic Fibrosis", *In the Metabolic and Molecular Basis of Inherited Disease,* C. R. Scriver, A. L. Beaudet, W. S. Sly, and D. Valle, eds. (New York: McGraw-Hill, Inc.), pp. 3799–3876). We now know that the disease is caused by mutations in the gene encoding the cystic fibrosis transmembrane conductance regulator (CFTR), a phosphorylation-regulated $Cl^-$ channel located in the apical membrane of involved epithelia. Also, much has been discovered about how CF-associated mutations disrupt protein function, thereby disrupting $Cl^-$ transport across CF epithelia.

Despite these advances, the pathogenesis of CF lung disease, the major cause of morbidity and mortality, is still not understood. Lung disease is characterized by bacterial colonization and chronic airway infection. Many organisms can be involved, but *Pseudomonas aeruginosa* and *Staphylococcus aureus* are particularly prominent (Konstan, M. W., (1993), "Infection and Inflammation of the Lung in Cystic Fibrosis", *In Cystic Fibrosis,* P. B. Davis, ed. (New York: Marcel Dekker, Inc.), pp. 219–276). Chronic bacterial infections progressively destroy the lung, and may ultimately lead to respiratory failure. Several hypotheses have been proposed to explain the pathogenesis of CF lung disease (Davis, P. B., (1993), "Pathophysiology of the Lung Disease in Cystic Fibrosis", *In Cystic Fibrosis,* P. B. Davis, ed. (New York: Marcel Dekker, Inc.), pp. 193–218; Wine, J. M., (1995), "How do CFTR Mutations Cause Cystic Fibrosis", *Curr. Biol.* 5, 1357–1359; Pilewski, J. M., (1995), "How do Cystic Fibrosis Transmembrane Conductance Regulator Mutations Produce Lung Disease?", *Curr. Opin. Pulm. Med.* 1, 435–443; Welsh, M. J., (1995), "Cystic Fibrosis", *In the Metabolic and Molecular Basis of Inherited Disease,* C. R. Scriver, A. L. Beaudet, W. S. Sly, and D. Valle, eds. (New York: McGraw-Hill, Inc.), pp. 3799–3876). However, it has been difficult to relate the characteristic disease abnormality, bacterial colonization and infection of airways, to the characteristic physiologic abnormality, defective transepithelial $Cl^-$ transport.

In other organs affected by CF, disease pathogenesis does not involve bacterial infections. For the sweat glands, pancreas, intestine, and male genital tract, plausible explanations of pathogenesis are based on defective transepithelial $Cl^-$ transport (Quinton, P. M., (1990), "Cystic Fibrosis: A Disease in Electrolyte Transport", *FASEB J.* 4, 2709–2717.; Welsh, M. J., (1995), "Cystic Fibrosis", *In the Metabolic and Molecular Basis of Inherited Disease,* C. R. Scriver, A. L. Beaudet, W. S. Sly, and D. Valle, eds. (New York: McGraw-Hill, Inc.), pp. 3799–3876). Likewise, as suggested by Quinton, P. M., (1984), "Exocrine Glands", *In Cystic Fibrosis,* L. M. Taussig, ed. (New York: Thieme-Statton Inc.), pp. 338–375 over a decade ago, defective transepithelial electrolyte transport might somehow be responsible for the pathogenesis of airway infections. In airway epithelia, the loss of CFTR $Cl^-$ channel function, perhaps combined with a secondary defect in $Na^+$ transport, leads to abnormal transepithelial salt and fluid transport (Boucher, R. C., (1983), "Epithelial Dysfunction in Cystic Fibrosis Lung Disease", *Lung* 161, 1–17; Jiang, C., (1993), "Altered Fluid Transport Across Airway Epithelium in Cystic Fibrosis", *Science* 262, 424–427; Smith, J. J. (1993), "Fluid and Electrolyte Transport by Cultured Human Airway Epithelia", *J. Clin. Invest.* 91, 1590–1597; Smith, J. M. (1994), "Defective Fluid Transport by Cystic Fibrosis Airway Epithelia", *J. Clin. Invest.* 93, 1307–1311). As a result, the composition of airway surface fluid is abnormal. Joris, L., (1993), "Elemental Composition of Human Airway Surface Fluid in Healthy and Diseased Airways", *Am. Rev. Respir. Dis.* 148, 1633–1637 and Gilljam, H., (1989), "Increased Bronchial Chloride Concentration in Cystic Fibrosis", *Scand. J. Clin. Lab. Invest.* 49, 121–124 have shown that airway surface fluid from patients with CF has increased concentrations of $Cl^-$ and $Na^+$ when compared to that of normal subjects. Until now, however, no one has been able to determine how these abnormal concentrations of ions correlates to increased airway infections in CF patients.

Applicants have now discovered that airway surface fluid in both normal and CF airway surfaces contains a defensin-like factor with broad-spectrum anti-microbial activity. The alteration of the ionic composition of airway surface fluid in CF patients inhibits the activity of this bactericidal factor which explains the increased frequency of airway infections in these patients. The discovery of this link between the abnormal ionic concentrations of airway surface fluid and increased infections provides valuable insight into local pulmonary defense mechanisms and for the prevention and treatment of airway infections in CF patients and in other disease states which are characterized by opportunistic respiratory infections.

It is therefore a primary objective of the present invention to provide a broad spectrum antimicrobial factor isolated from human mucosal epithelial cells.

It is a further objective of the present invention to provide a method of treating chronic airway infections characterized by defective ion transport.

It is another objective of the present invention to provide a method of purifying a broad spectrum antimicrobial factor isolated from human mucosal epithelial cells.

It is yet a further objective of the present invention to provide a therapeutic composition for treating pulmonary infections associated with CF by reducing the salt concentration of the airways in CF patients.

It is yet a further objective of the present invention to provide a method of preparing an antimicrobial composition containing a broad spectrum antimicrobial factor isolated from mucosal epithelial cells.

It is another objective of the present invention to provide a method of treating respiratory bacterial infections which are characterized by abnormal ion concentrations in airway surface fluid.

It is another objective of the present invention to provide a method of treating non-respiratory mucosal infections using a bactericidal factor isolated from mucosal epithelial cells.

It is yet another objective of the present invention to provide a method of testing for the presence of a broad spectrum antimicrobial factor using a sample from a biological source suspected of containing the antimicrobial factor.

Other objects of the invention will become apparent from the description of the invention which follows.

SUMMARY OF THE INVENTION

This invention relates to a broad spectrum antimicrobial factor which is produced by airway epithelial cells. This factor, which has been determined to be a defensin-like molecule, is present in the small amount of fluid covering the mucosal surface of airway cells. Importantly, this factor is active against a broad range of bacteria even in the absence of epithelial, inflammatory, or phagocytic cells. The factor is characterized as being a low molecular weight, heat-stable substance that has broad spectrum bactericidal activity, including *P. aeruginosa, E. coli*, and methicillin-resistant *S. aureus*. It has also shown activity against certain types of yeast and is expected to show broad specificity against yeast and other types of fungus. Its effectiveness is dependent on salt concentration, and in cystic fibrosis patients which have abnormal levels of salt concentration in the airways due to defective $Cl^-$ transport, the factor is inactivated leading for the first time to the explanation of the pulmonary infection associated with CF.

Thus the invention in one embodiment comprises a treatment for CF by re-activating the factor by decreasing salt concentration in airways of affected patients.

Applications for this bactericidal factor are numerous. First, the discovery of this unique factor can be used in the further study and understanding of cystic fibrosis. A fluid composition containing this factor is easily collected from the surface of airway epithelial cells. This composition can be used in in-vitro assays of epithelial cells to screen for agents which reverse the CF defect and re-activate the anti-microbial activity of the factor. The factor may be purified and formulated into a pharmacological preparation which may be used for preventing and treating pulmonary infections in susceptible persons not limited to CF patients. The factor may also be used to treat mucosal infections in other parts of the body, including urinary tract, vaginal, eye, gastrointestinal, and skin infections. The present invention further includes a method of preparing an antimicrobial composition containing the bactericidal factor.

BRIEF DESCRIPTION OF THE DRAWINGS

FIG. 12(A) is at low magnification. FIG. 12(B) shows an area of epithelium with a thin layer of material covering the apical surface. The bar indicates 3 μm.

DETAILED DESCRIPTION OF THE INVENTION

Despite an increased understanding of the cellular and molecular biology of the CFTR $Cl^-$ channels, it has not been previously known how defective $Cl^-$ transport across airway epithelia causes chronic bacterial infections in cystic fibrosis airways. The molecular defect in CFTR $Cl^-$ channels has now been linked to the pathogenesis of CF lung disease through a bactericidal factor found in the airway surface fluid of epithelial cells.

This factor plays an important role in maintaining an infection-free environment in normal airways. While both normal and CF airways contain this bactericidal factor, the high $Cl^-$ content of CF airways alters the composition of the airway surface fluid, thus inhibiting the bactericidal activity of the factor.

Figure 12A:
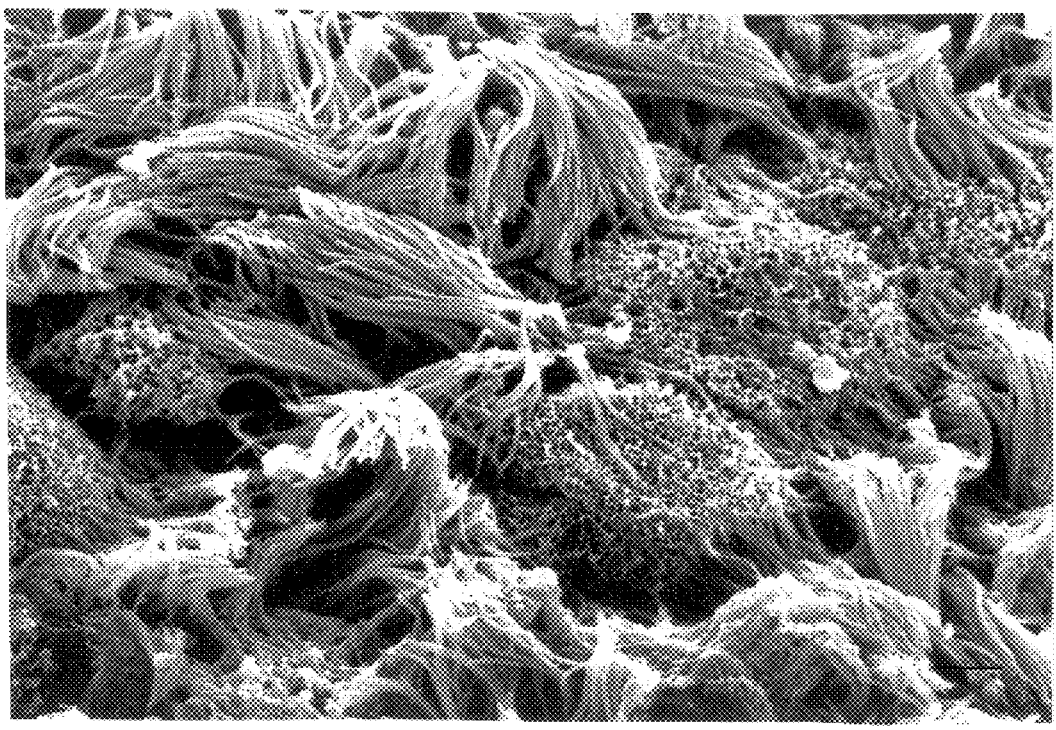
FIGS. 12(A) and 12(B) are scanning electron photomicrographs of the apical surface of cultured normal airway epithelium studied 41 days after seeding.
Figure 12B:
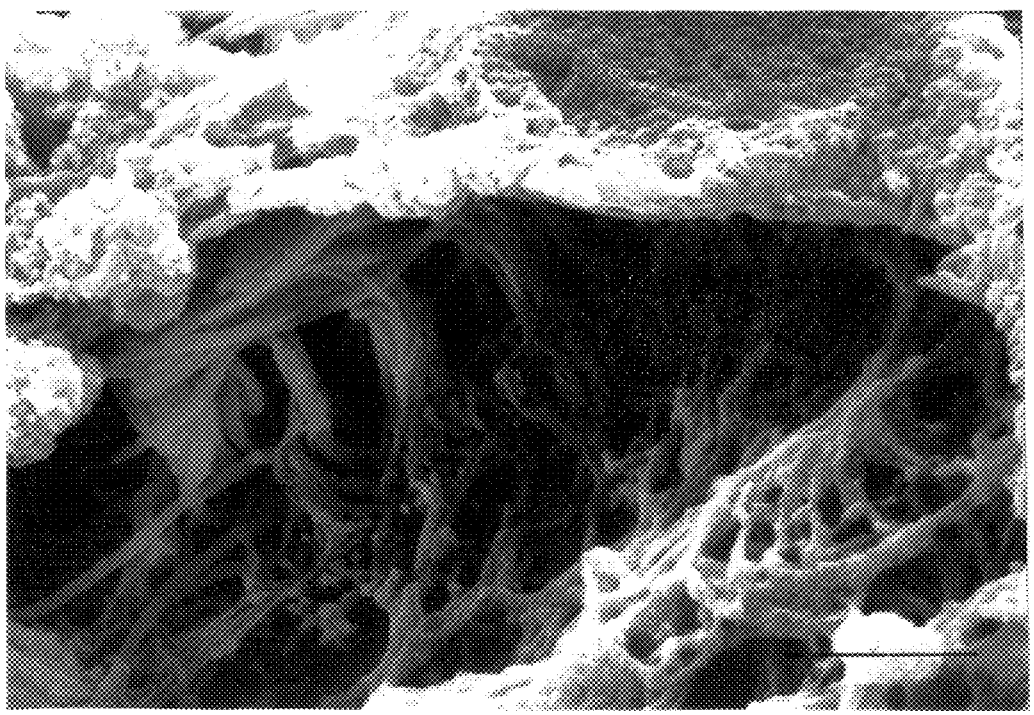

In one embodiment the invention comprises an assay for identifying or screening drugs or protocols which correct the factor inactivation associated with CF pulmonary infections. In vitro assays of epithelial cells have long been used and accepted in the art as predictive of in vivo responses. One such assay involves primary cultures of human airway epithelial cells. This model eliminates the antibacterial contribution of immune and inflammatory cells. First, the epithelial cells are cultured on permeable filter supports with air on the apical surface. With these conditions, the cells form a continuous, polarized sheet which develops a transepithelial electrical resistance and which actively transports $Na^+$ and $CL^-$ across the epithelium (Yamaya, M., (1992), "Differentiated Structure and Function of Cultures from Human Tracheal Epithelium", *Am. J. Physiol.* 262, L713–L724). Moreover, primary cultures of CF epithelia grown in this way manifest the CF defect in $Cl^-$ transport. Under these conditions, epithelia develop a ciliated apical surface resembling that observed in vivo (FIG. 12) (Breeze, R. G., (1977), "The Cells of the Pulmonary Airways", *Am. Rev. Respir. Dis.* 116, 705–777).

To mimic further the situation in vivo, bacteria could be inoculated directly onto the air-covered apical surface of normal airway epithelia using a small volume (20 nl). From this in vitro assay surface fluid may be collected which will contain the antimicrobial factor and can be used in further purification procedures known to those of skill in the art. Additionally the assay can be used to screen for drugs or protocols which will reverse the anti-microbial inactivation, simply by addition of the agent of interest and assay for antimicrobial activity as more fully described hereinafter.

In another embodiment the invention involves the preparation of a composition comprising the anti-microbial factor.

The bactericidal factor molecule can be purified from a variety of sources. For instance, the molecule can be extracted from airway epithelial cells by collecting the surface fluid. In addition, the factor can be extracted through the collection of bronchoalveolar lavage or by collection as supernatant from cultured epithelial cells.

In one embodiment of the invention, the bactericidal factor either purified or as a component of isolated surface fluid from either normal cells or CF cells, can be administered as a method of treating mucosal infections such as lung infections, for example, in CF, bronchitis, and in pneumonia. Further, the factor can be used in the prevention of pulmonary infections in people on ventilators, patients with tracheotomies, and patients with altered host immunity. The factor can also be used to treat blood borne infections. The factor is an endogenous chemical and will have little or no host response. The bactericidal factor is administered to the patient in a pharmaceutically acceptable form. Those skilled in the art of infectious disease will readily appreciate that the doses and schedules of the bactericidal factor will vary depending on the age, health, sex, size, and weight of the patient, the route of administration, the toxicity of the drugs and the relative susceptibilities of the infection to the bactericidal agent. These parameters can be determined for each system by well-established procedures and analysis e.g., in Phase I, II and III clinical trials.

In vitro tests conducted with purified defensins have demonstrated bactericidal activity at concentrations in the range of between 10 and 100 $\mu g/ml$. Lehrer et al., 1993, at 109. For in vivo use, the preferred dosage of the bactericidal factor is that which is necessary to attain a bactericidal concentration in blood of about 125 $\mu g/kg$ of body weight. Lehrer, et al., 1993, at 123.

For such administration, the bactericidal factor can be combined with a pharmaceutically acceptable carrier, such as a suitable liquid vehicle or excipient and an optional auxiliary additive or additives. The liquid vehicles and excipients are conventional and commercially available. Illustrative thereof are distilled water, physiological saline, aqueous solutions of dextrose and the like.

In general, in addition to the active compounds, the pharmaceutical compositions of this invention may contain suitable excipients and auxiliaries which facilitate processing of the active compounds into preparations which can be used pharmaceutically. Dosage may be administered to the lungs by aerosolization. Oral dosage forms encompass tablets, dragées, suspensions, solutions, and capsules. Preparations which can be administered rectally include suppositories. Other dosage forms include suitable solutions for administration parenterally or orally, and compositions which can be administered buccally or sublingually.

The pharmaceutical preparations of the present invention are manufactured in a manner which is itself well known in the art. For example, the pharmaceutical preparations may be made by means of conventional mixing, granulating, dragée-making, dissolving, or lyophilizing processes. The process to be used will depend ultimately on the physical properties of the active ingredient used.

Suitable excipients are, in particular, fillers such as sugars, for example, lactose or sucrose, mannitol or sorbitol, cellulose preparations and/or calcium phosphates, for example, tricalcium phosphate or calcium hydrogen phosphate, as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone. If desired, disintegrating agents may be added, such as the above-mentioned starches as well as carboxymethyl starch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate, and/or polyethylene glycol. Dragée cores may be provided with suitable coatings which, if desired, may be resistant to gastric juices.

For this purpose, concentrated sugar solutions may be used, which may optionally contain gum arabic, talc, polyvinylpyrrolidone, polyethylene glycol, and/or titanium dioxide, lacquer solutions, and suitable organic solvents of solvent mixtures. In order to produce coatings resistant to gastric juices, solutions of suitable cellulose preparations such as acetylcellulose phthalate or hydroxypropylmethyl-cellulose phthalate, are used. Dyestuffs and pigments may be added to the tablets of dragée coatings, for example, for identification or in order to characterize different combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition, stabilizers may be added. Possible pharmaceutical preparations which can be used rectally include for example, suppositories, which consist of a combination of the active compounds with a suppository base. Suitable suppository bases are, for example, natural or synthetic triglycerides, paraffin hydrocarbons, polyethylene glycols, or higher alkenyls. In addition, it is also possible to use gelatin rectal capsules which consist of a combination of the active compounds with a base. Possible base material include, for example, liquid triglycerides, polyethylene glycols, or paraffin hydrocarbons.

Suitable formulations for parenteral administration include aqueous solutions of the active compounds in water-soluble or water-dispersible form. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran, optionally, the suspension may also contain stabilizers.

In addition to administration with conventional carriers, the active ingredients may be administered by a variety of specialized delivery techniques. For example, the compounds of the present invention may also be administered encapsulated in liposomes, pharmaceutical compositions wherein the active ingredient is contained either dispersed or variously present in corpuscles consisting of aqueous concentric layers adherent to lipidic layers. The active ingredient, depending upon its solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, more or less ionic surfactants such as diacetylphosphate, stearylamine, or phosphatidic acid, and/or other materials of a hydrophobic nature. the diameters of the liposomes generally range from about 15 nm to about 5 microns.

The present invention also encompasses a method of treating not only respiratory infections, but also at other mucosal sites, for example, urinary tract, vaginal, gastrointestinal, and skin infections. Based on the similar physiology between all mucosal sites, it is expected that the bactericidal factor will also be effective at treating infections at these sites as well. Furthermore, if modified appropriately, the bactericidal factor could also be used to treat blood stream infections, infections of internal organs, and infections of the central nervous system.

In another embodiment of the invention, the discovery of the link between salt concentration in the surface fluid of the epithelial cells and bacterial infection can be used for a method of reducing the salt concentration of the surface fluid as a means of preventing infection. Salt-reducing agents, such as UTP would be one means of accomplishing this result. (Knowles, M. R., (1991), "Activation by Extracellular Nucleotides of Chloride Secretion in the Airway Epithelia of Patients with Cystic Fibrosis", *New Engl. J. Med.* 325, 533–538). Another method would be to increase the water concentration in the surface fluid to dilute the salt concentration. This can be accomplished using a nebulizer, for example. Moreover, the ionic salt concentration can also be reduced through the addition of nonionic molecules, such as sugar (e.g. mannitol, dextran, galactose), proteins and peptides (albumin) or lipids to the surface fluid.

A further embodiment of the invention includes a testing assay for CF protocols. Such an assay would involve subjecting the surface fluid from the mucosal or epithelial cells to an analysis of salt content. The assay could also be used to determine whether the supernatant is effective against the microbe as a means of detecting the presence of the factor. Further, the same assay can be used to test various substances which may reverse the effectiveness of the bactericidal factor.

The above experimental results link the molecular defect in CFTR $Cl^-$ channels to the pathogenesis of CF lung disease. More importantly, the data suggest novel assays for evaluating potential treatments and new approaches to CF therapy, as well as the treatment of other types of infection. The factor, once purified, could be altered to allow it to function at high salt concentration thus reversing the effects of CF. Methods for altering amino acid sequences to improve bioavailability or other pharmacological parameters is known to those of skill in the art. Additionally, other related anti-microbial factors could be isolated from different species to identify other closely related molecules, some of which might function at high salt concentration as determined by the method of the invention. In the case of gene therapy, knowledge of the relationship between the percentage of cells that express CFTR, the amount of CFTR expression per cell, and correction of the abnormal composition of airway surface fluid may help guide therapeutic trials. Isolation, characterization, and sequencing of this molecule are all accomplished according to standard protocols in the art; see, for example Maniantis et al, Molecular Cloning, 1988, Cold Spring Harbor Press, and will make possible mass production of this broad spectrum antibiotic, in such vehicles as bacterial cells, plant cells, or other eukaryotic cells. Transformation of plant cells with the gene encoding this factor may enable the plant to synthesize the factor which can be isolated therefrom. The following examples involve experiments conducted which demonstrate how the above-stated conclusions were reached. They are not meant to limit the present invention in any manner. All references to patents, journal articles, or other publications cited previously or hereinafter are hereby expressly incorporated in their entirety by reference.

GENERAL EXPERIMENTAL PROCEDURES

EXAMPLES 1–5

Culture of epithelia

Airway epithelial cells were isolated from nasal, tracheal, and bronchial epithelia from 5 CF and 14 normal (non-CF) people. Cells were seeded on collagen-coated, semipermeable membranes (0.6 cm$^2$), and grown at the air-liquid interface as previously described (Yamaya, M., (1992), "Differentiated Structure and Function of Cultures from Human Tracheal Epithelium", Am. J. Physiol. 262, L713–L724). Because primary cultures were being established, for 2–4 days after seeding the culture medium contained either 100 mU/ml penicillin plus 100 μg/ml streptomycin or the combination of penicillin, streptomycin, 50 μg/ml gentamicin, 40 μg/ml tobramycin, 15 μg/ml colimycin, 125 μg/ml ceftazidime, and 2 μg/ml fluconazole. Similar results were obtained with epithelia initially treated with either antibiotic mixture. After antibiotic treatment, the basolateral solution was replaced 5 times over 48 hours with antibiotic-free medium and the apical surface was washed 3 times over 48 hours with antibiotic-free phosphate-buffered Ringers solution. Thereafter, the antibiotic-free medium was changed at 2–3 day intervals. Epithelia were studied 8–45 days after seeding and showed bactericidal activity even after many changes in the basolateral solution and many washes over time of the apical solution. All epithelia used showed no leakage of fluid from the basolateral to the apical surface and paired monolayers had transepithelial resistances >500 Ω.cm$^2$. Epithelia were prepared for scanning electron microscopy using standard techniques.

In some studies, epithelia were treated with recombinant adenovirus to express CFTR. Previous studies have shown that Ad2/CFTR-8 (50 MOI) used under these conditions corrects the fluid and electrolyte transport defects in CF epithelia (Zabner, J., (1994), "Correction of cAMP-Stimulated Fluid Secretion in Cystic Fibrosis Airway Epithelia: Efficiency of Adenovirus-Mediated Gene Transfer In Vitro", Hum. Gene Ther. 5, 585–593; and Zabner and Welsh, unpublished). As a control, some epithelia were exposed to Ad2/βGal-2 which expresses β-galactosidase. As an additional control, one epithelium in each experiment was used to study the electrical properties to determine that cAMP-stimulated Cl$^-$ transport was corrected by treatment with Ad2/CFTR-8. Fisher rat thyroid epithelia were cultured as described (Sheppard, D. N., (1994), "Expression of Cystic Fibrosis Transmembrane Conductance Regulator in a Model Epithelium", Am. J. Physiol. 266, L-405–L413).

Bacterial stains and culture conditions

The bacteria used included: a laboratory strain of P. aeruginosa (PAO1S), a spontaneously occurring streptomycin-resistant mutant of the naturally ampicillin-resistant strain PAO1 (isolated by Dr. Charles Cox); E. coli HB101 (a streptomycin resistant strain); a Clinical isolate of P. aeruginosa (a mucoid strain from a CF patient); and a methicillin-resistant Clinical isolate of S. aureus. Bacteria were grown overnight in Luria broth. They were then washed 3 times in water, centrifuged at 4000× g for 15 minutes, and diluted in water to an appropriate density. The number of CFU were also measured directly in triplicate by plating 20 nl on Luria agar and counting colonies.

Application of bacteria to epithelia

A 20 nl drop of the bacterial suspension was applied to the apical or basolateral surface and epithelia were then incubated at 37° C. in a humidified cell culture incubator. After 24 hours, bacteria were recovered from epithelia by washing the apical surface with 60 μl of water (1–3 washes). Values greater than 1000 CFU were not determined and data are reported as >1000 CFU. However, in some cases where absolute counts were made, >10$^6$ CFU were present when we report >1000 CFU.

The 20 nl drop of bacteria was placed on the center of the epithelial monolayer and probably did not spread over the entire epithelium; therefore the relationship between the number of bacteria added, the area exposed, and the amount of antibacterial activity could not be determined.

In vitro studies of bactericidal activity

Airway surface fluid was collected by washing the apical surface of epithelia with 60 μl of water or an NaCl solution, as indicated. After pooling the recovered fluid, bacteria (in 20 nl of water) were added to 30 μl of the fluid and incubated at 37° C. for 3 hours. Under these in vitro conditions with airway surface fluid in water, P. aeruginosa were killed rapidly with a 50% decrease in viability in approximately 30 minutes (data not shown). The volume of airway surface fluid collected from the epithelia could not be determined but is very small, probably less than 1 μl. Bactericidal activity could not be attributed to the cell culture medium because bacteria multiplied when added to the basolateral medium (FIG. 2) or when added to a small amount of culture medium diluted in water (not shown). As described above, bactericidal activity could be removed from the epithelia by washing the surface. However, 24–48 hours after the apical surface was washed, epithelia recovered the ability to kill bacteria and bactericidal activity could once again be collected. In fact, bactericidal activity could be collected on several occasions over many days from a single epithelium.

Evidence that epithelia were not damaged by collection of surface fluid is: after washing, epithelia retained their transepithelial resistance and electrolyte transport properties: there was no leak of fluid from the basolateral to the apical surface; and 24 hours after washing bactericidal activity could again be recovered. Moreover, as described above and in FIG. 10, bactericidal activity could be recovered either with water or with a NaCl solution.

Collection and analysis of airway surface fluid from normal and CF subjects

Airway surface fluid was collected from 8 CF and 17 normal subjects. Before collection, subjects wore a nose Clip for 5 minutes to prevent breathing through the nose. Immediately after removing the nose Clip, a 0.32 cm$^2$ filter (66213, Gelman Sciences, Ann Arbor, Mich.) was gently applied to the inferior surface of the inferior turbinate. After 5 seconds the filter was withdrawn and immediately immersed in mineral oil to prevent evaporation. The mineral oil was not water saturated. Fluid was extracted from the filter as follows. The bottom of the microcentrifuge tube holding the filter in mineral oil was perforated and the tube was placed into a larger tube containing mineral oil. The tandem tubes were centrifuged at 174,000× g for 15 minutes to transfer the fluid into the larger tube without exposing it to air; the filter remained in the smaller microcentrifuge tube. Fluid samples collected from both nostrils of a subject were pooled and Cl$^-$ concentrations were measured by chloridimetry (Labconco Corp., Kansas City, Mo.). Control samples containing known Cl$^-$ concentrations were separated, stored and analyzed in an identical manner; in the control samples Cl$^-$ concentrations were always within 5 mM of the original concentration.

EXAMPLE 1

The first step in reaching the above-stated conclusions involved a study to determine what happens when bacteria are placed on normal airway epithelia. Human airways are continually exposed to bacteria in ambient air ($10^3/m^3$) and to aspirated bacteria (DeKoster, J. A. (1995), "Bioaerosol Concentrations in Non-Complaint, Complaint, and Intervention Homes in the Midwest", Am. Ind. Hyg. Assoc. J. 56, 573–580; Huxley, E. J., (1978), "Pharyngeal Aspiration in Normal Adults and Patients with Depressed Consciousness", Am. J. Med. 64, 564–568). Despite this exposure, the intrapulmonary airways remain sterile in healthy individuals.

Primary cultures of human airway epithelial cells were used as the model for these experiments. This model eliminates the antibacterial contribution of immune and inflammatory cells. First, the epithelial cells were cultured on permeable filter supports with air on the apical surface. With these conditions, the cells form a continuous, polarized sheet which develops a transepithelial electrical resistance and which actively transports $Na^+$ and $CL^-$ across the epithelium (Yamaya, M., (1992), "Differentiated Structure and Function of Cultures from Human Tracheal Epithelium", Am. J. Physiol. 262, L713–L724). Moreover, primary cultures of CF epithelia grown in this way manifest the CF defect in $Cl^-$ transport. Under these conditions, epithelia develop a ciliated apical surface resembling that observed in vivo (FIG. 12) (Breeze, R. G., (1977), "The Cells of the Pulmonary Airways", Am. Rev. Respir. Dis. 116, 705–777).

Figure 1:
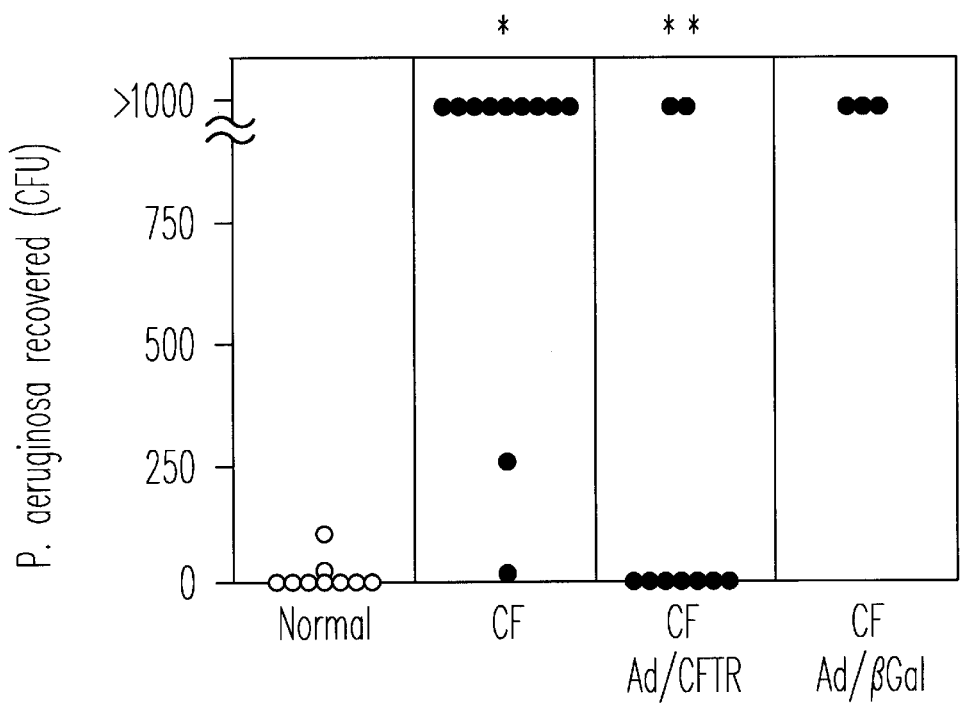
FIG. 1 is a graph depicting *P. aeruginosa* recovered from normal and CF epithelia 24 h after addition of 30–300 CFU. CF epithelia were treated with Ad2/CFTR-8 or Ad2/βGal-2 as indicated, 3–4 days before addition of *P. aeruginosa*. Each data point is from an individual epithelium. Asterisk indicated $p<0.0001$ compared to normal epithelia; double asterisk indicated $p<0.003$ compared to CF epithelia without Ad2/CFTR-8.

To mimic further the situation in vivo, bacteria were inoculated directly onto the air-covered apical surface of normal airway epithelia using a small volume (20 nl). 30–300 colony-forming units (CFU) of P. aeruginosa were then added to the surface and then placed the epithelia in a humidified cell culture incubator at 30° C. Twenty-four hours after the bacteria were added to the apical surface, either no P. aeruginosa were recovered or fewer than we had added (FIG. 1). Moreover, the epithelia remained viable and uninfected for as long as they were maintained afterward (up to 3 weeks).

Strikingly different results were obtained with CF airway epithelia (FIG. 1); 24 hours after adding P. aeruginosa to the apical surface, more bacteria were recovered than had been added. When CFTR was expressed in CF epithelia using a recombinant adenovirus, the defect in killing P. aeruginosa was corrected (FIG. 1). Treatment with a related adenovirus vector expressing β-galactosidase had no effect. This data indicates that airway epithelia possess an anti-Pseudomonas activity that is dependent on CFTR.

Figure 2:
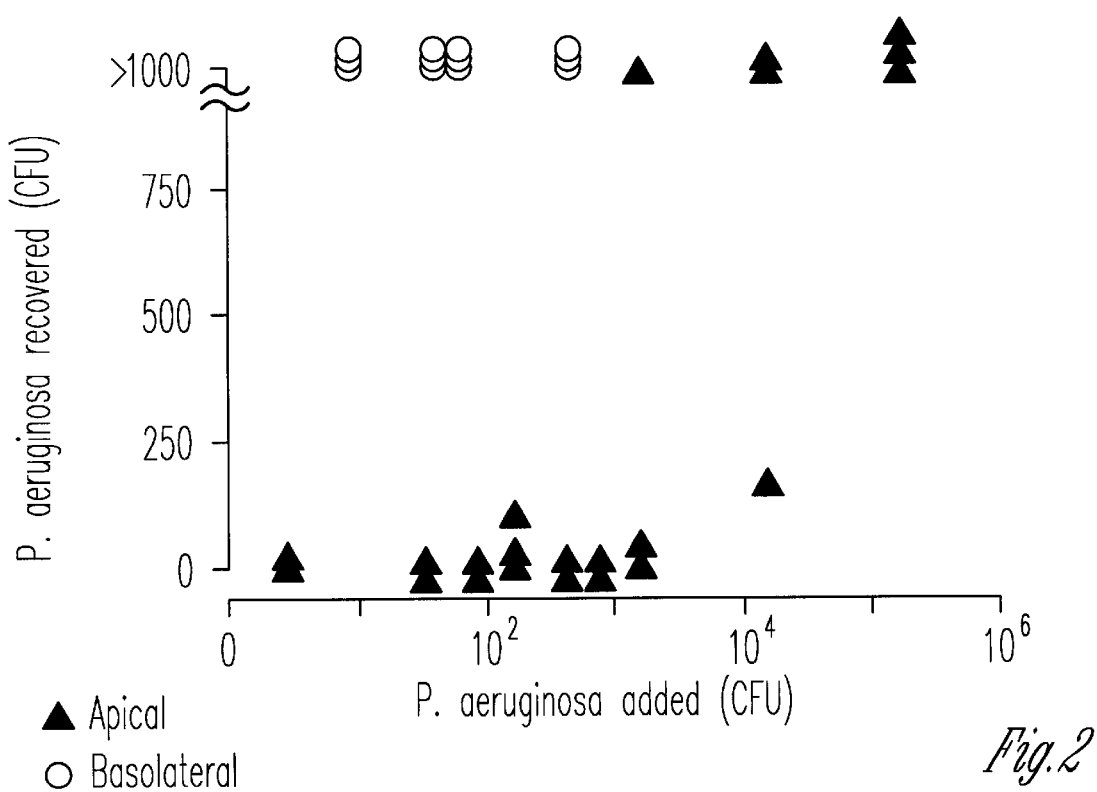
FIG. 2 is a graph depicting *P. aeruginosa* recovered after addition of indicated number of bacteria to the apical surface (Closed triangles) or basolateral solution (open circles). Data points indicate the total CFU recovered from each epithelium.

FIG. 2 shows that when up to $10^3$ P. aeruginosa were added to normal epithelia there were always fewer bacteria present 24 hours later. However, when more than $10^3$ P. aeruginosa was added, a greater number of bacteria was recovered 24 hours later, suggesting that the antibacterial system was overwhelmed. Yet when even a small number of bacteria were added to the basolateral solution, there was always profuse growth (FIG. 2), suggesting that the antibacterial activity was localized to the apical surface of the epithelia. Three hours after adding P. aeruginosa to the apical surface, the number of viable bacteria had decreased by about 50%. In contrast to airway epithelia, when less than 100 CFU of P. aeruginosa was added to the apical surface of Fisher rat thyroid epithelia, there was abundant growth (n=15, not shown).

Figure 3:
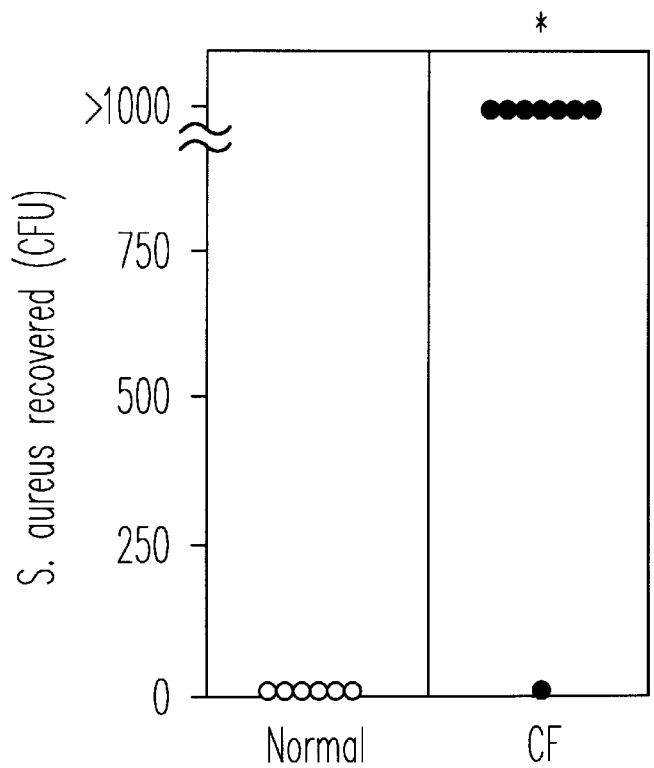
FIG. 3 is a graph depicting the amount of *S. aureus* recovered 24 h after addition of 70±8 CFU to the apical surface of normal or CF epithelia. Asterisk indicates $p<0.02$.

The airways of CF patients are colonized by many different bacteria; S. aureus is often one of the first organisms detected (Ramsey, B. W., (1991), "Predictive Value of Oropharyngeal Cultures for Identifying Lower Airway Bacteria in Cystic Fibrosis Patients", Am. Rev. Respir. Dis. 144, 331–337; Konstan, M. W., (1993), "Infection and Inflammation of the Lung in Cystic Fibrosis", In Cystic Fibrosis, P. B. Davis, ed. (New York: Marcel Dekker, Inc.), pp. 219–276). FIG. 3 shows that normal epithelia also killed a methicillin-resistant Clinical isolate of S. aureus added to the apical surface. Again, in contrast to normal epithelia, S. aureus multiplied on the surface of CF epithelia. Thus, based upon the above studies, the conclusion reached was that normal but not CF epithelia kill bacteria applied to the apical surface.

EXAMPLE 2

Figure 4:
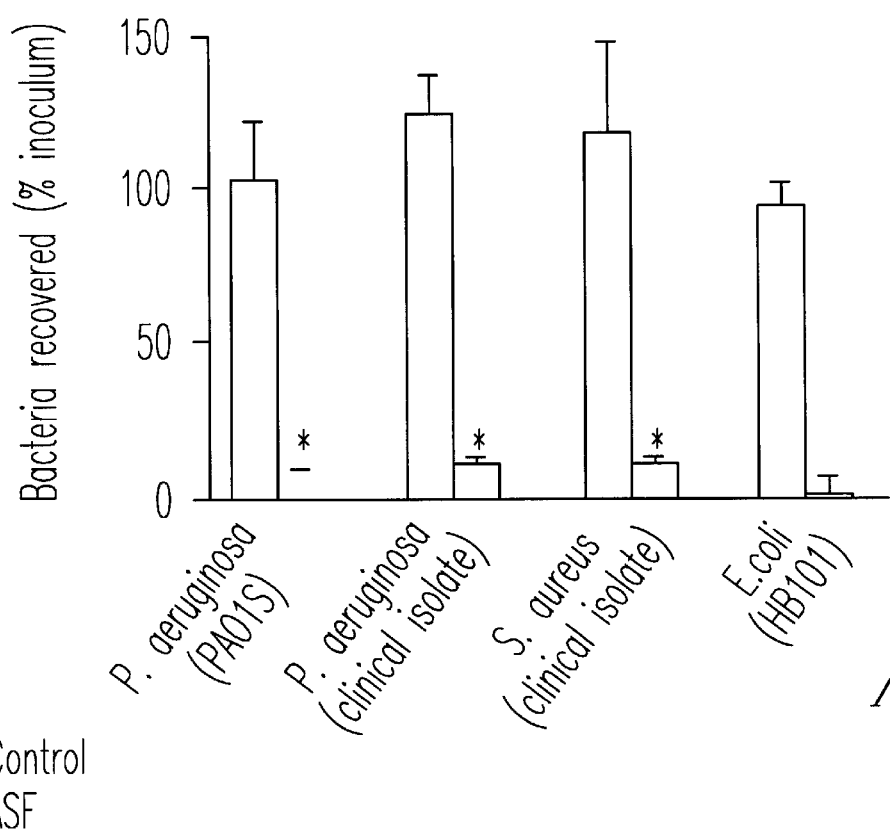
FIG. 4 is a graph depicting bacteria recovered after incubation in airway surface fluid (ASF) collected in water from normal epithelia. *P. aeruginosa* PAO1S (49±9 CFU), a clinical isolate of *P. aeruginosa* (69±19 CFU), a clinical isolate of *S. aureus* (58±9 CFU), or *E. coli* HB101 (351±115 CFU) were incubated in water (control) or airway surface fluid in water (ASF) at 37° C. for 3 h. Data are mean±SEM; n=3 for each point. Asterisk indicated $p<0.006$ compared to control.
Figure 5:
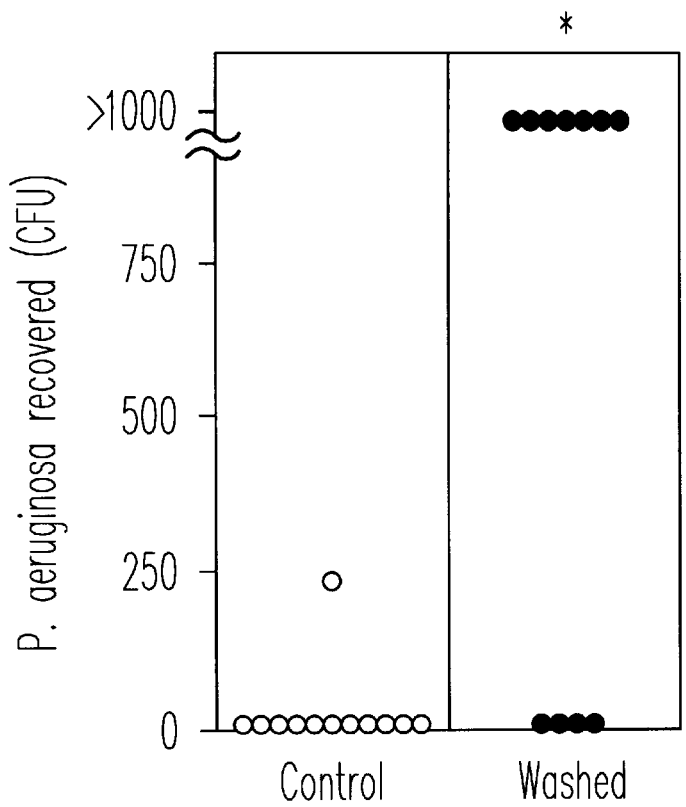
FIG. 5 is a graph depicting *P. aeruginosa* recovered 24 h after addition to normal epithelia as described in legend of FIG. 1 or to epithelia in which the apical surface had been washed before addition of bacteria. Asterisk indicated $p<0.01$.
Figure 6:
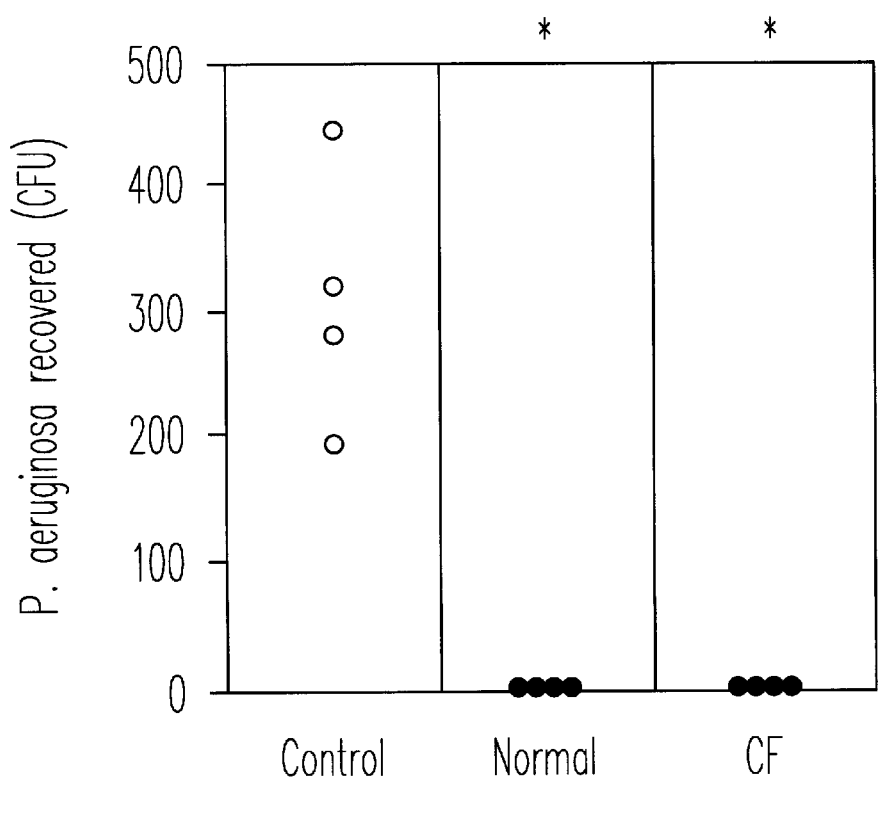
FIG. 6 is a graph depicting *P. aeruginosa* (665±75 CFU) was added to water alone (control) or to airway surface fluid collected in water from CF or normal airway epithelia and incubated at 37° C. for 3 h. Similar results were obtained in 3 other sets of experiments in which 25–70 CFU were added. Asterisk indicates $p<0.001$ compared to control.

Because bacteria were killed after addition to the small amount of fluid covering the apical surface of normal epithelia, the next question was whether this airway surface fluid had bactericidal activity. Airway surface fluid was collected by washing the apical surface with water and then adding P. aeruginosa to the recovered fluid. Fluid recovered from normal airway surfaces killed P. aeruginosa (FIG. 4). Conversely, immediately after washing the apical surface, epithelia lost the ability to kill P. aeruginosa (FIG. 5). Airway surface fluid also killed Escherichia coli, and Clinical isolates of P. aeruginosa and methicillin-resistant S. aureus (FIG. 6). These results demonstrated that airway surface fluid contains broad-spectrum bactericidal activity.

Without wishing to be bound by any theory the broad spectrum of bactericidal activity suggested that surface fluid might contain a defensin-line factor (Lehrer, R. I., (1993), "Defensins: Antimicrobial and Cytotoxic Peptides of Mammalian Cells", Annu. Rev. Immunol. 11, 105–128; Martin, E., (1995), "Defensins and Other Endogenous Peptide Antibiotics of Vertebrates", J. Leukoc. Biol. 58, 128–136). Microfiltration experiments indicated that the bactericidal factor was smaller than 10 kD; airway surface fluid that had passed through a Microcon-10 filter (Amicon, Beverly, Mass.) had anti-Pseudomonas activity equal to that of unfiltered airway surface fluid (n=12). In addition, boiling the fluid for 10 minutes did not abolish its activity as compared to unboiled fluid (n=12). A low molecular weight and heat-stability are characteristic of defensins (Lehrer, R. I., (1993), "Defensins: Antimicrobial and Cytotoxic Peptides of Mammalian Cells", Annu. Rev. Immunol. 11, 105–128; Martin, E., (1995), "Defensins and Other Endogenous Peptide Antibiotics of Vertebrates", J. Leukoc. Biol. 58, 128–136).

Because bacteria multiplied on the surface of CF epithelia, the question raised was whether the bactericidal factor was missing in CF. Interestingly, airway surface fluid collected in water from either normal or CF epithelia, killed P. aeruginosa (FIG. 6). This finding indicates that CF epithelia do not lack a bactericidal factor and, thus, both normal and CF airway surface fluids contain bactericidal activity. Hence, the conclusion reached was that CF epithelia fail to kill P. aeruginosa (FIG. 1) because the composition of airway surface fluid is altered and this inhibits the activity of a bactericidal factor.

EXAMPLE 3

Figure 7:
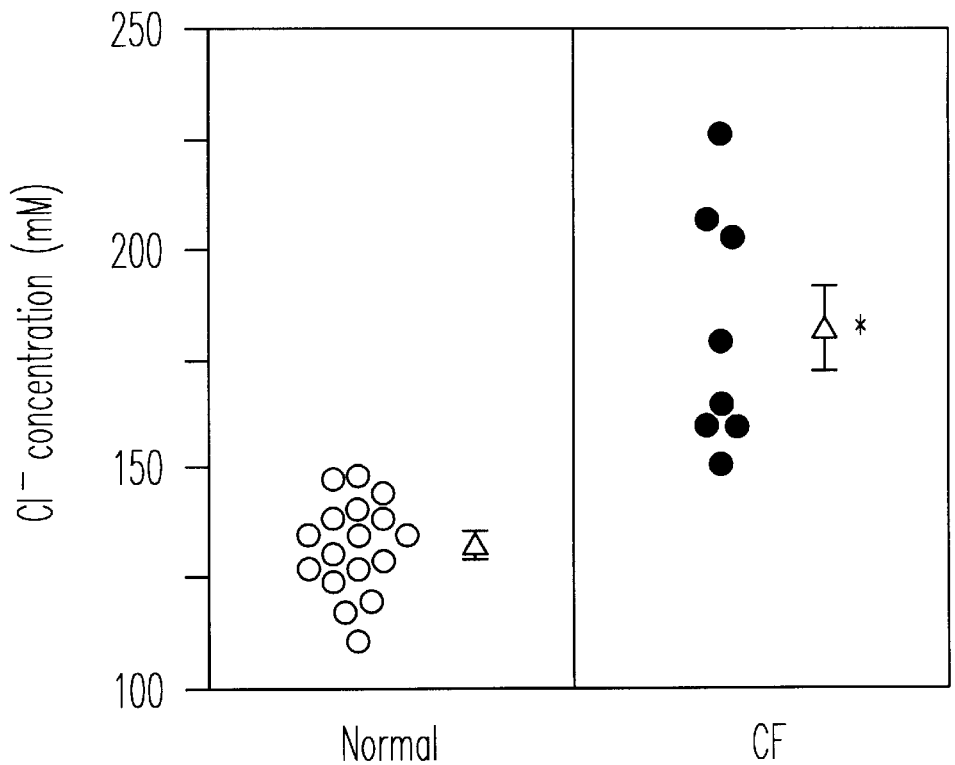
FIG. 7 is a graph depicting the concentration of $Cl^-$ in airway surface fluid collected from nasal epithelium of CF (n=8) and normal (n=17) subjects. Each point is the value from an individual subject; mean±SEM are indicated. Asterisk indicates $p<0.001$ compared to normal.

The differences between CF surface fluid and normal surface fluid were therefore the next avenue of study. Joris, L., (1993), "Elemental Composition of Human Airway Surface Fluid in Healthy and Diseased Airways", Am. Rev. Respir. Dis. 148, 1633–1637 and Gilljam, H., (1989), "Increased Bronchial Chloride Concentration in Cystic Fibrosis", *Scand. J. Clin. Lab. Invest.* 49, 121–124 used bronchoscopy to obtain airway surface fluid from the trachea and main stem bronchi of normal and CF subjects. They found that normal fluid had Cl$^-$ concentrations of 84±9 mM and 85±54 mM, respectively, whereas CF fluid had higher Cl$^-$ concentrations of 129±5 mM and 170±79 mM. To confirm this difference, the Cl$^-$ concentration in airway surface fluid obtained from the nasal mucosa was measured. Nasal mucosa was used because the function and histology of the epithelium is similar to that of intrapulmonary airways and it is easily accessible. As in the earlier reports, the data showed that the Cl$^-$ concentration in CF fluid (182±10 mM) was higher than in normal fluid (132±3 mM) (FIG. 7). Evaporation and/or methodological differences may account for the fact that higher Cl$^-$ concentrations were found in nasal fluid than were reported in tracheal fluid (Joris, L., (1993), "Elemental Composition of Human Airway Surface Fluid in Healthy and Diseased Airways", *Am. Rev. Respir. Dis.* 148, 1633–1637 and Gilljam, H., (1989), "Increased Bronchial Chloride Concentration in Cystic Fibrosis", *Scand. J. Clin. Lab. Invest.* 49, 121–124).

The above results demonstrated that airway surface fluid from CF epithelia has an abnormally increased Cl$^-$ concentration. This may occur because the loss of CFTR Cl$^-$ channels prevent Cl$^-$ from accompanying Na$^+$ absorption, much as occurs in CF sweat ducts (Quinton, P. M., (1990), "Cystic Fibrosis: A Disease in Electrolyte Transport", *FASEB J.* 4, 2709–2717; Quinton, P. M., (1994), "Viscosity Versus Composition in Airway Pathology", *Am. J. Respir. Crit. Care Med.* 149, 6–7).

EXAMPLE 4

Figure 8:
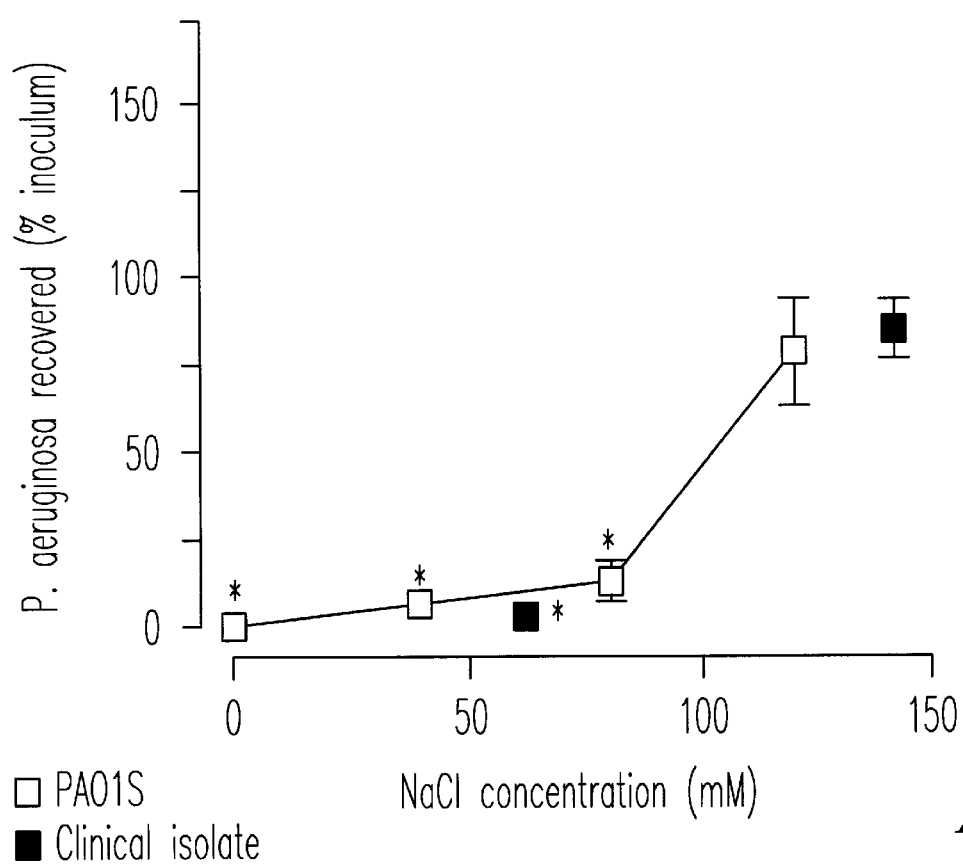
FIG. 8 is a graph depicting the bactericidal activity of airway surface fluid collected in either water or the indicated concentration of NaCl. Data are means ±SEM of the bacteria recovered (as a percent of inoculum) 3 hours after the addition of 49±9 CFU P. aeruginosa PAO1S or 38±4 CFU of a Clinical isolate of P. aeruginosa.
Figure 9:
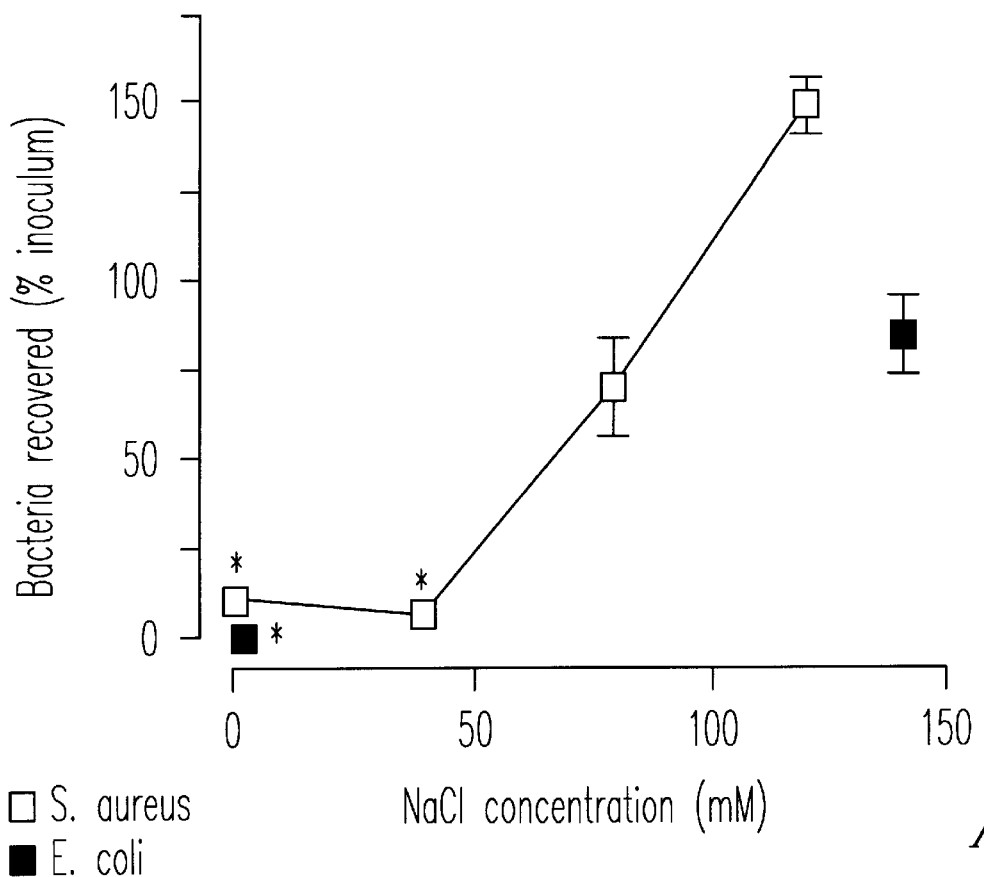
FIG. 9 is a graph depicting the bactericidal activity of airway surface fluid collected as in FIG. 8 after the addition of 58±9 CFU of a Clinical isolate of S. aureus or 351±115 CFU E. Coli HB101; n=3 for each point. Asterisk indicates values significantly less than the amount added (p<0.005).

To determine whether the electrolyte concentration could affect bactericidal activity, airway surface fluid was removed with solutions containing different concentrations of NaCl and the ability of the fluid to kill bacteria in vitro was then tested. As the concentration of NaCl increased, anti-Pseudomonas activity decreased (FIG. 8). Similar results were obtained with Clinical isolates of *P. aeruginosa* and *S. aureus,* and with *E. coli* (FIGS. 8 and 9). This data demonstrates that increased electrolyte concentrations reduce bactericidal activity.

Figure 10:
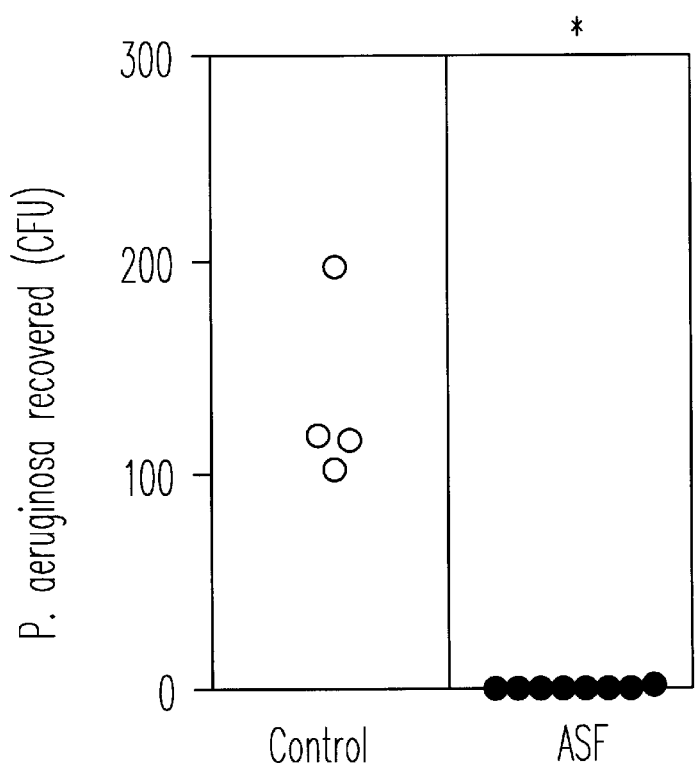
FIG. 10 is a graph depicting airway surface fluid which was collected by washing the apical surface of normal epithelia with 60 μl of 140 mM NaCl. This solution was then diluted 1:2 with water (final NaCl concentration, 47 mM). Data are P. aeruginosa recovered after 3 h incubation at 37° C. control indicates salt solution (47 mM NaCl) containing no airway surface fluid. Asterisk indicates value different from control, p<0.001.

Bactericidal activity was also present when airway surface fluid was collected with 140 mM NaCl (instead of with water) and then diluted the fluid to a NaCl concentration of 47 mM before adding *P. aeruginosa* (FIG. 10). This data demonstrates that although the electrolyte composition affects bactericidal activity, it does not affect the ability to recover the bactericidal factor from the airway surface.

EXAMPLE 5

Figure 11:
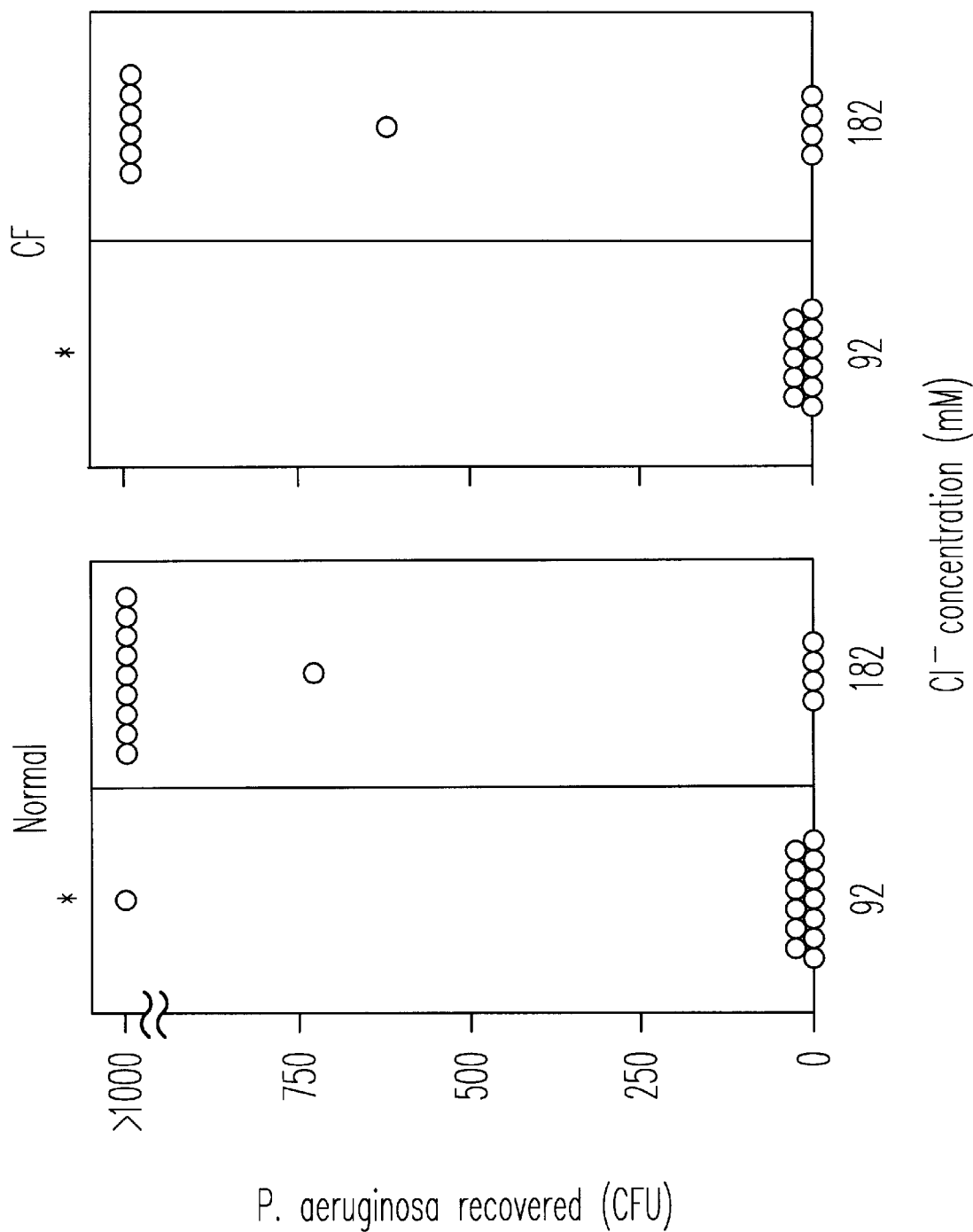
FIG. 11 is a graph depicting the effect of Cl$^-$ concentration on the bactericidal activity of normal and CF epithelia. The apical surface of epithelia was covered with 60 μl of a solution containing 1 mM CaCl$_2$, 20 mM KCl, and either 70 or 160 mM NaCl (total Cl$^-$ concentration indicated for each data bin). The basolateral solution (culture media) was diluted with water to minimize transepithelial osmotic gradients. Epithelia were incubated for 24 h after addition of P. aeruginosa (325±54 CFU). In separate experiments, after 24 h the Cl$^-$ concentration on the apical surface remained within 6 mM of the starting concentration. Each data point is from a separate epithelium. Asterisk indicates p<0.003 compared to 182 mM Cl$^-$.

The above results show that CF epithelia produce a bactericidal factor that fails to kill bacteria applied to their apical surface because the surface fluid has an abnormally high salt concentration. Thus it was concluded that if the electrolyte concentration on the airway surface was altered, bactericidal activity would also be altered. To test this conclusion, a small amount of solution (60 μl) with a known salt concentration was applied to the apical surface of normal and CF airway epithelia and *P. aeruginosa* was then added. When *P. aeruginosa* was added to normal epithelia covered with a solution containing a low Cl$^-$ concentration, the bacteria were killed. (FIG. 11). This result is the same with direct addition of *P. aeruginosa* to the airway surface (FIG. 1). However, with a high salt concentration on the apical surface of normal epithelia, the bacteria multiplied. Thus increasing the salt concentration caused normal epithelia to behave like CF epithelia. Most importantly, when the salt concentration was reduced, bacteria placed on CF epithelia were killed (FIG. 11). Thus, a reduction of the NaCl concentration allows CF epithelia to kill *P. aeruginosa*.

Figure 13A:
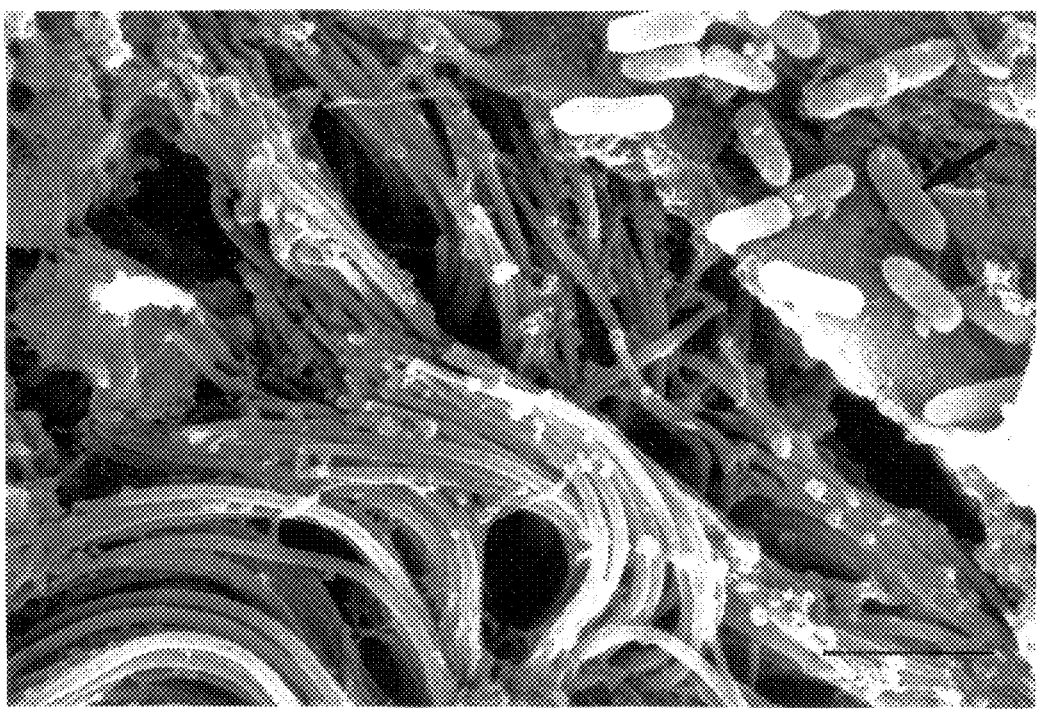
FIGS. 13(A) and 13(B) are scanning electron photomicrographs of the surface of CF epithelia. P. aeruginosa (PAO1S 459±47 CFU) was added 48 h before processing. Epithelia were covered with 60 μl of a solution containing either 182 mM Cl$^-$ [FIG. 13(A)] or 92 mM Cl$^-$ [FIG. 13(B)] as described in FIG. 11. Bacteria were usually found on a thin film of material with a mucus-like appearance. Cilia are visible beneath the thin film of material. Arrow indicates P. aeruginosa. Bar indicates 3 μm.
Figure 13B:
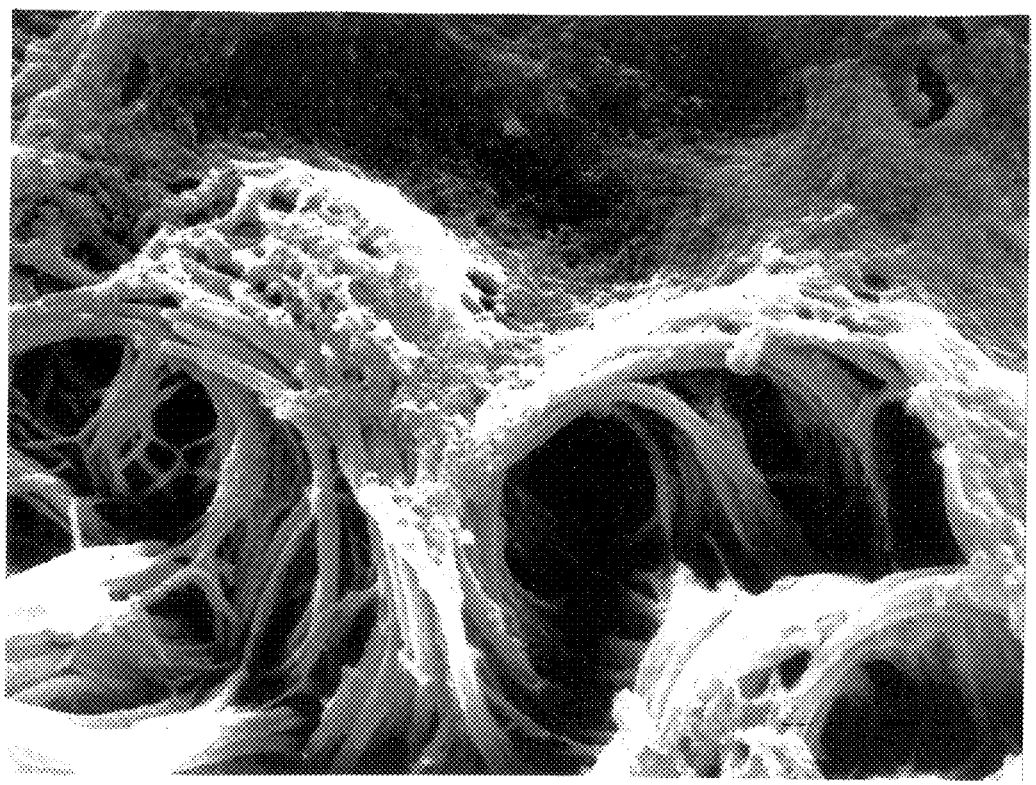

Scanning electron photomicrographs confirmed these results. *P. aeruginosa* was added to CF epithelia covered with a thin layer of solution containing either 182 mM Cl$^-$ or 92 mM Cl$^-$. Forty-eight hours after their addition to epithelia with a high salt concentration, *P. aeruginosa* was observed on the apical surface (FIG. 13, top photo). In contrast, bacteria could not be found on CF epithelia when the salt concentration was low (FIG. 13, bottom photo).

The above data provides a link between the physiologic hallmark of CF, defective transepithelial Cl$^-$ transport, and the Clinical hallmark of CF, airway infections with CF pathogens like *P. aeruginosa* and *S. aureus*. The results demonstrate that airway epithelia secrete a bactericidal substance into the thin layer of fluid covering the apical surface where its activity depends on a low salt concentration. In CF epithelia, loss of CFTR Cl$^-$ channels produces an abnormally high salt concentration in the airway surface fluid which reduces bactericidal activity. When the salt concentration is lowered, CF epithelia can kill *P. aeruginosa.*

Bactericidal activity in the airway surface fluid may be the first line of defense that protects the lung from bacteria and helps maintain a sterile intrapulmonary environment. Loss of this activity explains lung disease in patients with CF as follows. Bacteria deposit on the airway surface after inhalation and aspiration. Normally, they would be killed by bactericidal activity in airway surface fluid. However, this system is impaired in CF. As a result, a second line of defense, neutrophils and macrophages may kill the bacteria and release cytokines that recruit additional neutrophils, thereby generating an inflammatory environment (Wilmott, R. W., (1990), "Increased Levels of Interleukin-1 in Bronchoalveolar Washings From Children with Bacterial Pulmonary Infections", *Am. Rev. Respir. Dis.* 142, 365–368; Davis, P. B., (1993), "Pathophysiology of the Lung Disease in Cystic Fibrosis", *In Cystic Fibrosis,* P. B. Davis, ed. (New York: Marcel Dekker, Inc.), pp. 193–218; Konstan, M. W., (1993), "Infection and Inflammation of the Lung in Cystic Fibrosis", *In Cystic Fibrosis,* P. B. Davis, ed. (New York: Marcel Dekker, Inc.), pp. 219–276; Goldstein, I. M. (1994), "Host Defenses in the Lung: Neutrophils, Complement, and Other Humoral Mediators". *In Testbook of Respiratory Medicine,* J. F. Murray and J. A. Nadel, eds. (Philadelphia: W. B. Saunders), pp. 402–418).

Without wishing to be bound by any theory, it is believed that the bactericidal factor produced by airway epithelia may be a novel defensin-like molecule because it has several properties characteristic of such factors (Lehrer, R. I., (1993), "Defensins: Antimicrobial and Cytotoxic Peptides of Mammalian Cells", *Annu. Rev. Immunol.* 11, 105–128; Martin, E., (1995), "Defensins and Other Endogenous Peptide Antibiotics of Vertebrates", *J. Leukoc. Biol.* 58, 128–136) since it is a low molecular weight, heat-stable substance that has broad-spectrum bactericidal activity and its killing is dependent on salt concentration. In addition, expression of a defensin has been detected in bovine airway epithelial cells (Diamond, G., (1993), "Airway Epithelial Cells are the Site of Expression of a Mammalian Antimicrobial Peptide Gene", *Proc. Natl. Acad. Sci. U.S.A.* 90, 4596–4600). Identification of the bactericidal factor and elucidation of its mechanism of action provides additional insights into local pulmonary defense mechanisms and could lead to the development of more effective bactericidal agents.

Further features of the identified bactericidal factor include its mechanism of killing which is different from most currently available antibiotics. For example, the bactericidal factor not only kills gram positive bacteria like *S. Aureus* and gram negative bacteria like *P. aeruginosa* and *E. coli*, but also bacteria which are resistant to ampicillin, methicillin, and streptomycin. Further, preliminary data also demonstrates that the molecule shows activity against yeast.

Because the bactericidal factor is a naturally occurring molecule, it will not induce an immune or allergic response. In addition, it is not toxic to cells in vivo or in tissue culture.

Purification of the bactericidal factor can be achieved using the purification procedures which have been used for other defensins and which are well known in the art (Lehrer et al., "Defensins: Antimicrobial and Cytotoxic Peptides of Mammalian Cells," *Annu. Rev. Immunol.* 1993. 11: 105–28, the disclosure of which is herein incorporated by reference). Purification has been accomplished by a combination of techniques, including size exclusion, ion exchange, and hydrophilic interaction, chromatography, preparative gel electrophoresis and reversed phase high performance liquid chromatography. The bactericidal factor is preferably purified using microfiltration and reverse-phase HPLC, the procedures of which are well known in the art.

EXAMPLE 6

Figure 14:
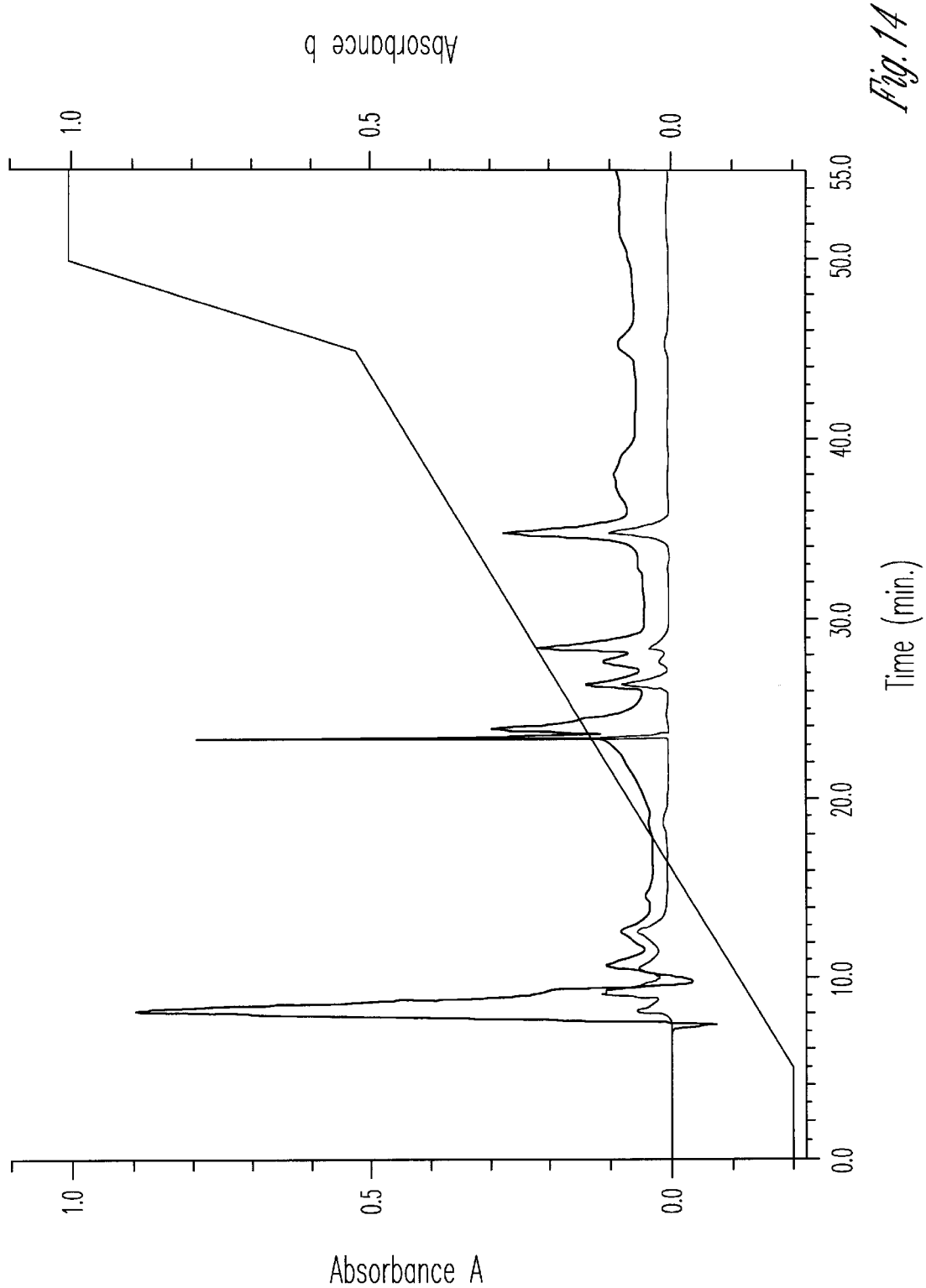
FIG. 14 is a graph of the absorbance spectrum of HPLC purification of the antibacterial factor of the invention.

The factor was purified using microfiltration and reverse-phase HPLC. Active factor which is inhibited by high concentrations of sodium chloride has been consistently recovered. The factor is inhibited by other salts, but not by high concentrations of uncharged molecules (such as galactose); this result suggests that the factor is inhibited by high ionic strength rather than by high osmolarity. FIG. 14 depicts an absorbance spectrum of HPLC purification of the factor. Airway surface liquid was collected from monolayer cultures of human airway epithelia. After low-speed centrifugation, the supernatant was passed through a Centricon 10 microfiltration unit. The filtrate was concentrated and applied to a PRP-3 Reversed Phase HPLC column (Hamilton Co., Reno, Nev.). The mobile phases used were solvent A (o.1% trifluoroacetic acid, 99.9% $H^2O$) and solvent B (0.1% trifluoroacetic acid, 60% acetonitrile, 30% isopropanol, 9.9% $H^2O$). Molecules were eluted with a linear gradient from 0 to 60% solvent B in 40 min, followed by a linear gradient from 60% to 100% B in 5 min. The flow rate was 1 ml/min, and absorbance was monitored at 220 nm (solid line) and 280 nm (dashed line). Fractions were collected and assayed for antibacterial activity. Antibacterial activity eluted between 8–9 min and corresponds to a major peak that absorbs at 220 nm.

It is therefore submitted that the present invention accomplishes at least all of its stated objectives.

EXAMPLE 7

Previously, the antibacterial factor was removed from cultures of human airway epithelia grown on small permeable supports at the air-liquid interface. The apical surface of the epithelium was washed with a small volume of water and it was shown by colony counting methods that bacteria added to the isolated material were killed. Most of the studies involved killing relatively small numbers of *P. aeruginosa*, the most common CF pathogen. However, because the antibacterial factor is obtained from primary cultures of human airway epithelia, supplies are limited. Thus it was difficult to examine the activity in detail. A more sensitive and less cumbersome quantitative assay than the colony counting assay was developed. The assay is based on the correlation between luminescence and viability of a recombinant strain of *Escherichia coli*.

Bacterial Strains, Plasmid, and Culture Conditions.

The bacteria used were *E. coli* DH5α (GIBCO-BRL Life Technologies, Grand Island, N.Y., and *P. aeruginosa* PAO1, Holloway, B. W. (1955) *J Gen Micro*, 13: 572–581. The luminescence plasmid used was pCGLS1, Frackman, S, (1990) *Journal of Bacteriology*, 172: 5767–5773. This plasmid is a ColE1 replicon containing the luxCDABE operon from *Photorhabdus luminescens* and an ampicillin resistance marker. *Escherichia coli* was grown in Luria-Bertani broth, Sambrook, J., (1989) "Molecular Cloning: A Laboratory Manual", (Cold Spring Harbor Laboratory Press, Cold Spring Harbor, N.Y.) and *P. aeruginosa* in trypticase soy broth (Difco Laboratories, Detroit, Mich.), both at 30° C. with shaking. Solid media for colony counting experiments contained 1.5% agar. For maintenance of pCGLS1, ampicillin (100 µg/ml) was included in the growth medium.

Airway Surface Fluid. Fluid was washed from the apical surface of cultured airway epithelia with distilled water as described previously. Smith, J. J., (1996) *Cell*, 85: 229–236. For all experiments on the effects of salt and osmolites, a pooled stock containing 3.3 units of antibacterial activity per 1 µl was used (see later for the definition of a unit of activity). The pooled sample was obtained by washing epithelia repeatedly at 48 hour intervals. Although there was variability in the absolute quantity of antimicrobial factor washed from individual epithelial layers, experiments with other samples of ASF yielded similar results. In some studies inflammatory mediators were added to the apical surface of the epithelium for 19 hours before collection of airway surface fluid (ASF). These included lipopolysaccharide (50 µg/ml, Sigma), interleukin-6 (10 ng/ml, generously provided by G. Hunninghake), c5a (20 nM, Sigma), and Na butyrate (5 mM, Sigma).

Bacterial Viability Experiments. The influence of ASF on bacterial viability was measured using a modification of the procedure described previously. Smith, J. J., (1996) *Cell*, 85: 229–236. Unless otherwise indicated, cultures in the logarithmic phase of growth were diluted in 33 µl of 1% (v/v) Luria-Bertani broth containing ASF. The number of bacteria, time, and temperature of incubation were as indicated. Colony-forming units were determined by standard plate counting procedures.

Influence of ASF on Luminescence of *E. coli* Containing pCGLS1. Cultures grown to a density of approximately $10^9$ cells per ml were diluted 100-fold in 10 mM potassium phosphate buffer (pH 7.4) with 1% Luria-Bertani medium. One-hundred ml of cell suspension plus 75 ml of any additional materials in deionized water were added to wells of a 96-well polystyrene OptiPlate (Packard, Downers Grove, Ill.). Thus each well contained approximately $10^6$ bacteria in a volume of 175 ml. The plates were incubated at 30° C., and luminescence was monitored with a microtiter dish luminometer (Lucy 1, Anthos Labtec, Salzburg, Austria). Luminescence is reported as relative light units.

Figure 15:
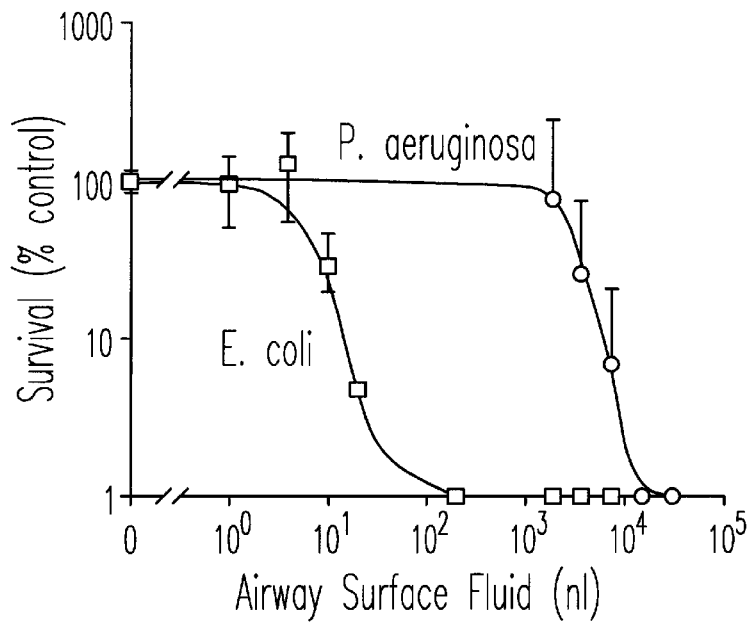
FIG. 15 is a graph of the Sensitivity of P. aeruginosa PAO1 (○) and E. coli DH5α(□) to ASF. The percentage of viable cells after 3 hours at 37 C. in a total volume of 33 μl was determined. The indicated amounts of ASF were added. The number of viable cells was determined by a plate count method, and the ASF was from a pooled stock as described in the Materials and Methods. Symbols represent the mean of measurements and bars indicate the range of values. E. coli DH5α results are the average of two assays done in triplicate, P. aeruginosa PAO1 results are from one assay done in triplicate.

Results of the Luminescence Assay. In a general screen of bacterial species we found that a common laboratory strain of *E. coli*, DH5α, was relatively sensitive to the antibacterial factor in ASF (S. Travis, J. Smith, and B. Conway, unpublished data). FIG. 15 shows a comparison of the sensitivity of *P. aeruginosa* PAO1 and *E. coli* DH5α to the antibacterial activity. Killing of *E. coli* required about 100-fold less ASF than did killing of *P. aeruginosa*. Because a sensitive indicator organism would allow us to conserve the limited available quantities of ASF, we chose to develop the luminescence assay with *E. coli* DH5α.

Because bacterial luminescence requires cellular energy (for recent reviews see Forst, S. (1996) *Microbiological Reviews* 60: 21–43; Meighen, E. (1991) *Microbiological Reviews* 55: 123–142), the amount of luminescence is related to the number of living bacterial cells. The luminescence genes from several bacterial species have been cloned and characterized. Baldwin, T. O., (1984) *Biochemistry*, 23: 3663–3667; Engebrecht, J., (1984) *Proc. Natl Acad Sci USA*, 81: 4154–4158; Szittner R., (1990) *The Journal of Biological Chemistry*, 265: 16581–16587. We used those from *Photorhabdus luminescens* because these genes are expressed well in *E. coli* and the luciferase from this organism is more heat stable than luciferases from other luminescent bacteria. Szittner R., (1990) *The Journal of Biological Chemistry*, 265: 16581–16587. As previously reported, we found the highest levels of luminescence in the late logarithmic phase of growth. Frackman, S., (1990) *Journal of Bacteriology*, 172: 5767–5773. Thus for maximal sensitivity, it was important to use cells from cultures at a density of about $10^9$ cells per ml. We performed all experiments at 30° C. because *E. coli* containing pCGLS1 produced considerably more light at 30° C. than at 37° C.

Figure 16:
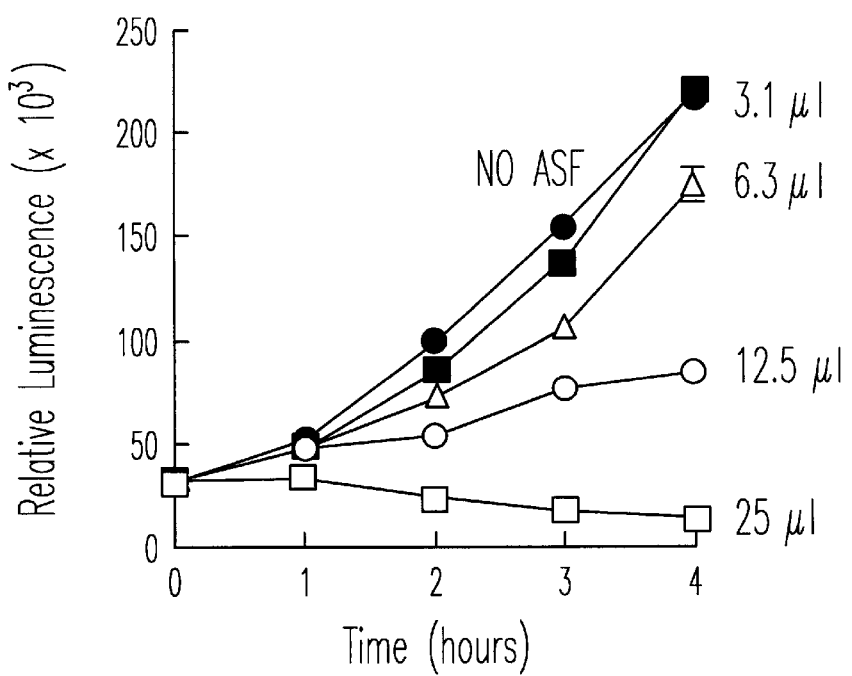
FIG. 16 is a graph demonstrating that the Luminescence of E. coli DHSA containing pCGLS1 is decreased by ASF in a dose-dependent manner. Luminescence is expressed as relative light units (RLU) in the presence of the following amounts of ASF per 175 μl reaction: 25 μl of ASF (□), 12.5 μl (○), 6.3 μl (△), 3.1 μl (■), and no ASF (●). The ASF used in this experiment was obtained by washing a single epithelial layer; similar results were obtained in at least two other assays. Symbols represent the mean of duplicate measurements and bars (where large enough to be visible) indicate the range of values.
Figure 17:
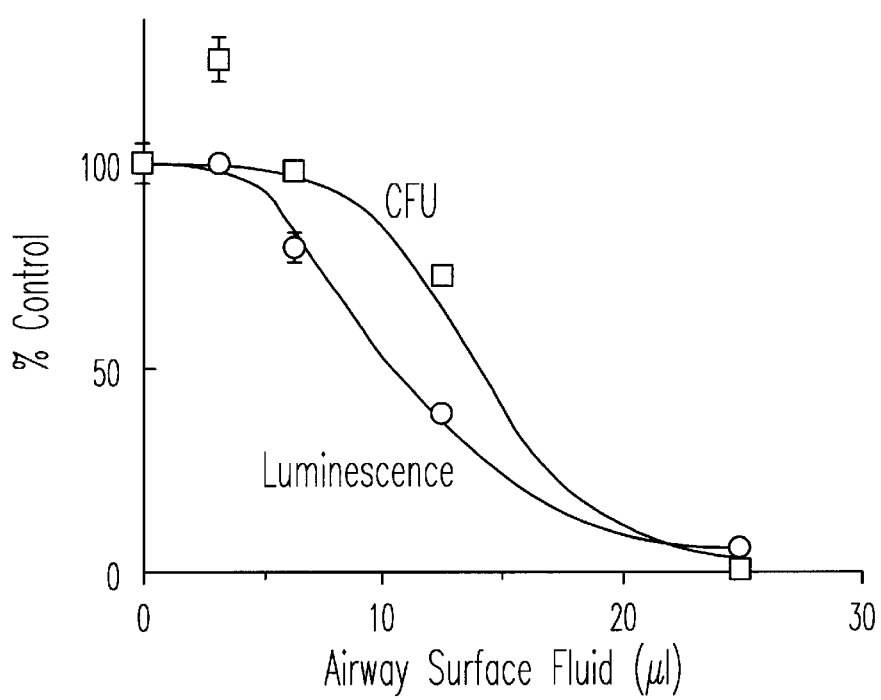
FIG. 17 is a graph depicting the relationship between luminescence (circles) and viability (squares) of E. coli DH5α containing pCGLS1. Viability of cells in which luminescence was determined was determined by plate counting. Values are percent of control in absence of ASF. Incubation time was 4 hours; nearly identical results were obtained with a 3 hour incubation. Symbols represent the mean of duplicate (luminescence) or triplicate (CFU) measurements and bars indicate the range of values. Abbreviations: Lum, luminescence; CFU, colony forming units.

When we incubated bacteria without ASF, luminescence slowly increased with time, consistent with limited growth (FIG. 16). However, in the presence of ASF, luminescence decreased or increased more slowly, depending on the concentration of ASF. The data show that luminescence was inversely related to the amount of ASF added to the cell suspension. To determine whether the decrease in luminescence was related directly to viability, we measured the amount of luminescence and compared it to the number of viable cells determined by the plate counting assay (FIG. 17). At varied amounts of ASF there was a good correlation between luminescence and viability of *E. Coli* containing pCGLS1.

Figure 18:
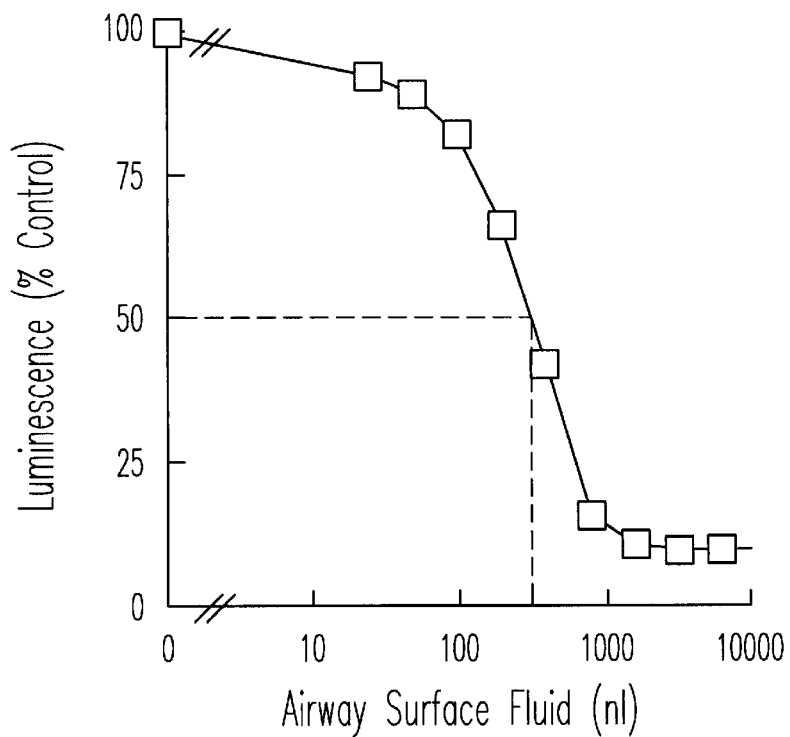
FIG. 18 is a graph depicting the effect of increasing amounts of ASF on luminescence. Luminescence is shown as percentage of the value obtained in the absence of ASF. Volume of ASF added to the assay (final volume 150 μl) is indicated. By definition 1 unit of activity corresponds to about 300 nanoliters of ASF (dotted lines). Symbols represent the mean of duplicate measurements and bars indicating range are hidden by symbols; similar results were obtained in at least two other assays.

FIG. 18 shows the relationship between the amount of ASF in the reaction and antibacterial activity. There was little decrease in luminescence at low concentrations of ASF, a sharp drop in luminescence over a range of 100 to 1000 nl of fluid per 175 µl assay mixture, and a residual amount of luminescence with higher concentrations of ASF. To standardize subsequent experiments, we defined the amount of the antibacterial factor required to decrease luminescence by 50% in the absence of added salt as 1 unit (dashed lines in FIG. 18). Thus the pooled ASF used in this and all subsequent experiments contained approximately 1 unit of antibacterial factor in 300 nl of ASF. However, we noted some variability in the concentration of factor in sampling from one day to another and from one epithelium to another. For example, the ASF used in the experiment shown in FIGS. 16 and 17 contained 0.3 units per 1 µl. We do not know the source of all of the variability, but it could be due in part to the efficiency of washing a very small volume of fluid from the epithelial surface.

Figure 19:
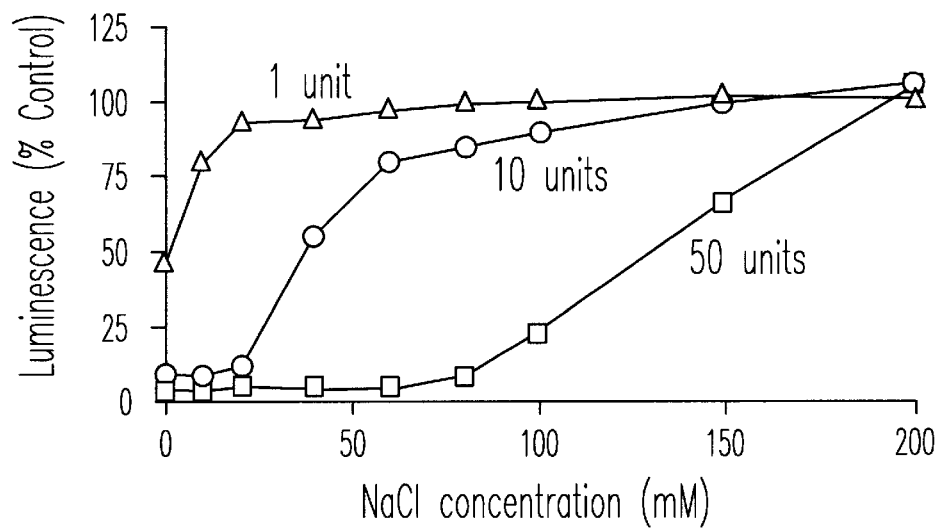
FIG. 19 is a graph depicting the relationship between amount of antibacterial factor and NaCl concentration on luminescence. Values are percentage of the value obtained at indicated concentrations of NaCl in the absence of ASF. One unit (□), 10 units, (○), and 50 units (□) of the antibacterial factor were added to assay (final volume was constant at 175 μl). Symbols represent the mean of duplicate measurements from a single assay and bars indicating range are hidden by symbols.

Effect of NaCl and Amount of ASF on Activity of the Antibacterial Factor. In a previous report we showed that the antibacterial factor was inhibited by high concentrations of NaCl. Smith, J., (1996) *Cell*, 85: 229–236. We hypothesized that the factor might be an important first line of defense against airway infections, and might be defective in CF due to elevated NaCl concentrations. Thus it is important to understand how elevated concentrations of $Na^+$ and $Cl^-$ inhibit activity of the antibacterial factor. We asked about the relationship between the concentration of NaCl, the concentration of the antibacterial factor, and the activity of the antibacterial factor. We found that the inhibitory effect of salt could be partially overcome when we added more units of the antibacterial factor (FIG. 19). For example, relatively low concentrations of NaCl (20 mM) completely inhibited the antibacterial activity of 1 unit of the factor but had little if any effect on 50 units. However, 50 units of the antibacterial factor were completely inhibited by higher NaCl concentrations (200 mM). The effect of salt on 10 units of the factor showed an intermediate level of inhibition. As a reference, two studies in which $Cl^-$ was measured in normal and CF ASF showed that the $Cl^-$ concentration in normal fluid averaged about 85 mM and that in CF fluid averaged about 130 mM in one study (Joris, L., (1993) *American Review of Respiratory Disease* 148: 1633–1637) and approximately 170 mM in another (Gilljam, H., (1989) *Scand. J. Clin. Lab Invest* 49: 121–124).

Figure 20:
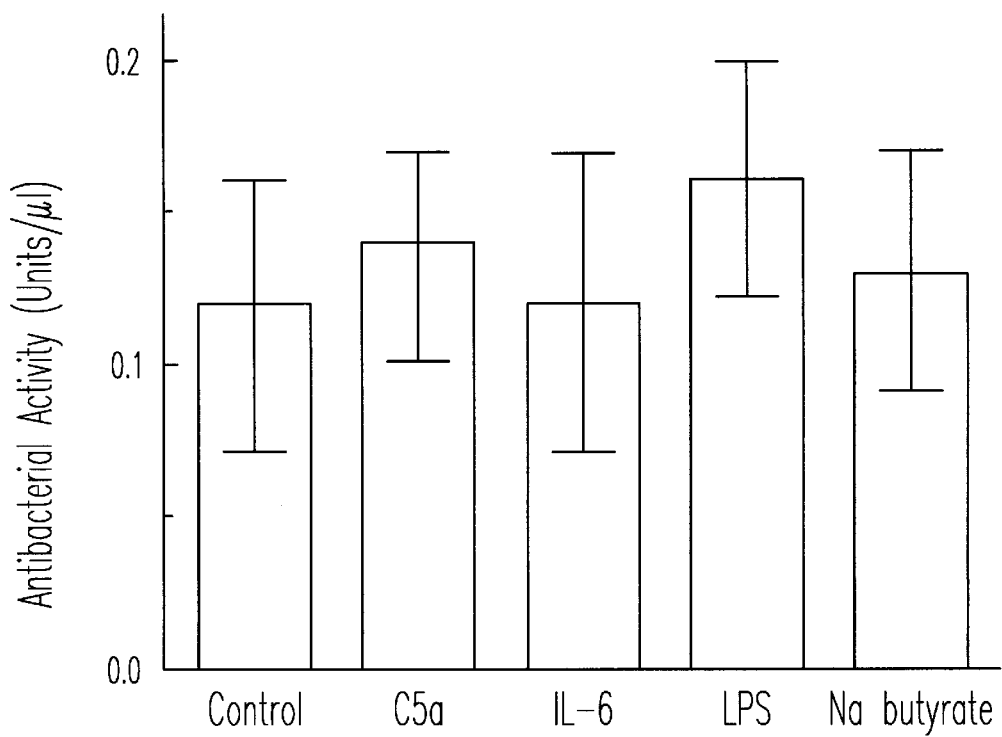
FIG. 20 is a graph depicting the effects of inflammatory modulators on amount of antibacterial factor in ASF. Epithelia were rinsed with water, then stimulated for 33 hours with the indicated agent added to the apical surface. Concentrations used were IL-6 (10 ng/ml), LPS (50 μg/ml), Na butyrate (5 nM), and C5a (20 nM). ASF was collected after 33 hours and assayed with the luminescence assay. Collection of fluid 19 hours after addition of the reagents produced similar results. Data represent the mean of triplicate measurements from a single assay and bars indicate range.

The fact that the inhibitory effect of salt could be partially overcome by larger amounts of the antibacterial factor suggested that stimulating factor production might be a reasonable strategy to increase bacterial killing in the human airway. Previous work with two other antibacterial factors, the bovine β-defensins TAP and LAP, showed that inflammatory mediators increased transcripts of TAP and LAP in bovine airway epithelia. Diamond, G., (1996) *Proceedings of the National Academy of Sciences USA* 93: 5156–5160; Schonwetter, B., (1995), *Science* 267: 1645–1648. Therefore we tested lipopolysaccharide (LPS, 50 µg/ml) and interleukin-6 (IL-6, 10 ng/ml). The C5a receptor is involved in mucosal defense in mouse airway (Hopken, U. E., (1996) *Nature* 383: 86–88), so we tested the effect of C5a (20 nM). We also tested the effect of Na butyrate (5 mM), a nonspecific stimulator of transcription. FIG. 20 shows that none of these interventions increased the antibacterial activity in ASF. Although the number of agents tested was small, these data suggest that inflammatory mediators may not increase the amount of antimicrobial factor in human airway and therefore tend to distinguish it from the bovine β-defensins TAP and LAP.

Figure 21A:
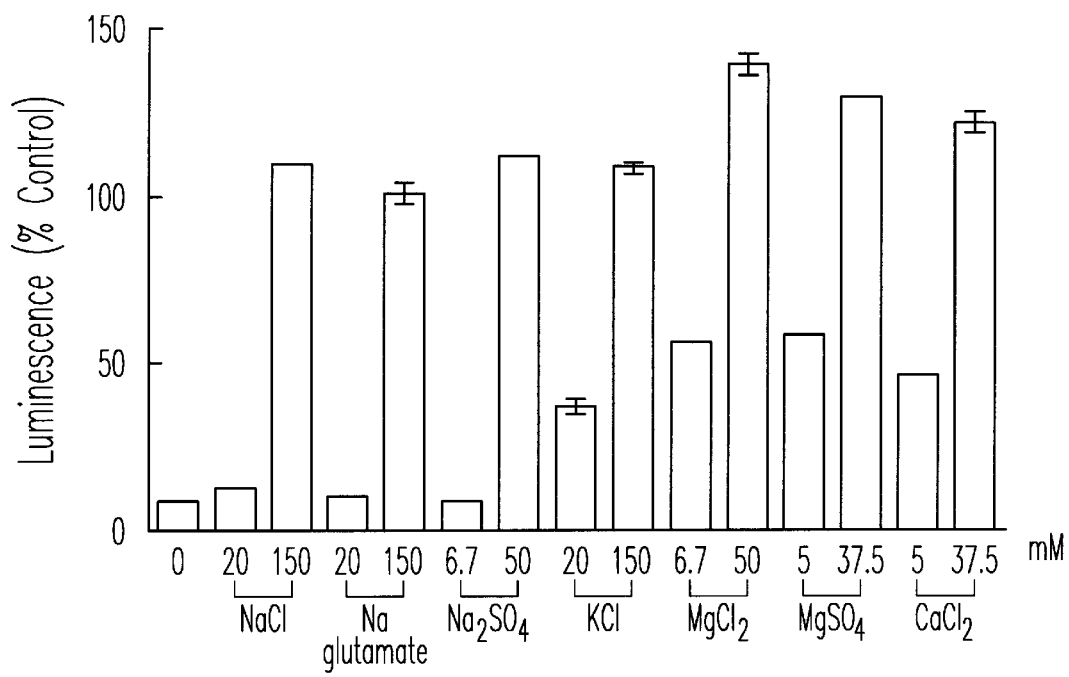
FIGS. 21A and 21B are graphs depicting the effect of ionic and nonionic osmolites on the antibacterial activity of ASF. (A) Replacement of Na$^+$ and Cl$^-$ with other ions. (B) Replacement of NaCl with nonionic osmolites. Because there is a small stimulation of light production by salt, values are percentage of luminescence with each salt or nonionic osmolite at the indicated concentration in the absence of ASF. Data represent the mean of at least duplicate measurements and bars (where large enough to be visible) indicate range.

Influence of Fluid Composition on Antibacterial Activity of ASF. An important set of questions is whether specific ions inhibit the antibacterial factor or whether inhibition results from high ionic strength or high osmotic strength. As shown in FIG. 21A, the activity of 10 units of antibacterial factor was inhibited by 150 mM, but not 20 mM NaCl. Inhibition by Na glutamate and $Na_2SO_4$ were indistinguishable from inhibition by NaCl, suggesting that there was no specific requirement from $Cl^-$ in inhibition. At low concentrations (20 mM), KCl appeared to be a slightly more effective inhibitor than NaCl. When $Na^+$ was replaced by the divalent cations $Mg^{2+}$ or $Ca^{2+}$, there was significant inhibition of antibacterial activity at low concentrations (5–6.7 nM), whereas 20 mM NaCl had little effect. These experiments suggest that there is no absolute requirement for specific ions. However the data also suggest that divalent cations are more effective inhibitors than monovalent cations.

Figure 21B:
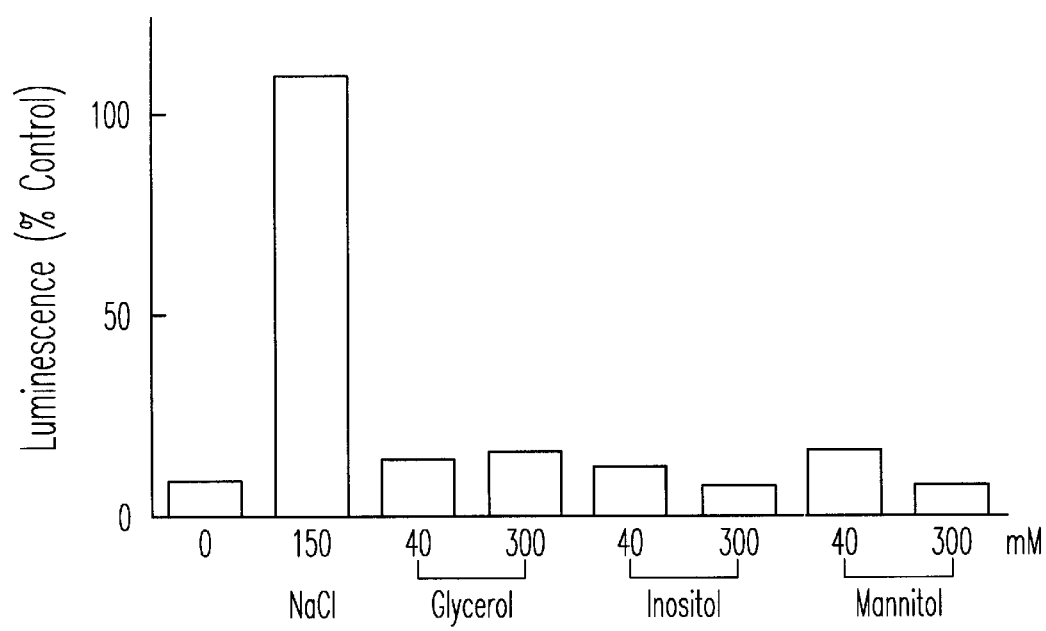

The effect of divalent cations suggested that inhibition was related to salt, perhaps cations, and was not a function of osmotic strength. To test directly this hypothesis, we examined the effect of nonionic osmolites. To compare the data to the effect of 150 mM NaCl, we used an approximately equivalent osmotic strength (300 mM) of several nonelectrolytes. FIG. 21B shows that none of the nonionic osmolites we tested inhibited the activity of the antibacterial factor. This result indicates that the antibacterial factor is sensitive to ionic, but not osmotic, strength.

Here we describe a simple, sensitive, quantitative, and rapid bioluminescence assay that can be used to measure the antibacterial activity of this factor in very small quantities of ASF. This assay should provide an important tool in attempts to purify the substance(s) that produces antibacterial activity in human airways.

The antibacterial activity of ASF has characteristics similar to many naturally occurring antibacterial peptides. Ganz, T. (1995) *Parmac Ther,* 66: 191–205. It is small, cationic, resistant to heat (Smith, J., (1996) *Cell* 85: 229–236 and FIG. 5) and it is salt-sensitive. Our data indicate that the activity is sensitive to ionic strength rather than osmolarity, and suggest that inhibition may be primarily a function of cations. Cations, especially divalent cations, also inhibit the activity of cationic antibacterial peptides against gram-negative bacteria. Ganz, T. (1995) *Pharmac Ther* 66: 191–205; Nicas, T., (1980) *Journal of Bacteriology* 143: 872–878. Apparently, the cations compete for binding sites on the lipopolysaccharide surface of the outer membrane. Ganz, T. (1995) *Pharmac Ther* 66: 191–205; Nicas, T., (1980) *Journal of Bacteriology* 143: 872–878. Thus our results on salt inhibition are consistent with the idea that the antibacterial factor in ASF may be a cationic peptide.

Implications for Therapy. The data suggest two possible approaches for preventing or treating bacterial colonization in the CF lung. First, the data shows that inhibition of the antibacterial factor by NaCl can be partially compensated by increased amounts of antibacterial factor.

Second, our data suggest that any treatment that decreases the salt concentration in CF ASF might allow the factor to kill bacteria. Our finding that isosmotic concentrations of nonionic osmolites do not inhibit the antibacterial factor suggest that they might be used to draw water to the apical surface of epithelia thereby diluting the concentrations of $Na^+$ and $Cl^-$, thus allowing greater activity of the antibacterial factor.

EXAMPLE 8

Cell culture, collection of ASF and defensins. Human airway epithelia were grown on collagen-coated, permeable filter supports (Transwell, Millipore) at the air-liquid interface (Smith, J. J., et al, 1996, "Cystic fibrosis airway epithelia fail to kill bacteria because of abnormal ASF", *Cell,* 85: 229–236; Zabner, J, et al, 1996, "Adenovirus-mediated gene transfer to ciliated airway epithelia requires prolonged incubation time", *J Virol,* (In Press)). T84 cells were grown as described (Anderson, M. P. et al, 1991, "Calcium and cAMP activate different chloride channels in the apical membrane of normal and cystic fibrosis epithelia", *Proc. Natl. Acad. Sci. USA,* 88: 6003–6007). Human neutrophils were a generous gift of Dr. William Nauseef and Jan Renee.

ASF was collected as described (Smith, J. J., et al, 1996, "Cystic fibrosis airway epithelia fail to kill bacteria because of abnormal ASF", *Cell,* 85: 229–236) except 400 µl of water was used to wash each epithelial surface. To determine the best schedule for ASF collection, we examined production of the antibacterial factor with time. When ASF was collected each day for 3 days, activity in each sample decreased; when epithelia were allowed to recover for 1 day between collections, activity returned to the original levels. Therefore, we collected fluid 3 times a week.

Antimicrobial Assays. We used three antimicrobial assays to measure activity; each assay has advantages and disadvantages as described below.

Plating assay. The plating assay is a widely-used, but laborious, technique for measuring antimicrobial activity against a variety of organisms. The bacteria used were: *Escherichia coli* DH5α, *Pseudomonas aureus* (PAO1S) (Smith, J. J., et al, 1996, "Cystic fibrosis airway epithelia fail to kill bacteria because of abnormal ASF", *Cell,* 85: 229–236); and clinical strains of *Burkholderia cepacia, Streptococcus pneumoniae,* methicillin-resistant *Staphylococcus aureus,* and *Serratia marcesens.* Bacteria were grown overnight in an appropriate medium, diluted 1:10, and grown to log phase. *Candida albicans* (ATCC 10237) was grown in Sabouraud-dextrose medium. Cells were collated by centrifugation and suspended in 10 mM potassium phosphate pH 7.4. Generally, 2000–5000 cfu/ml were added to ASF and other additions in a final volume of 33 µl containing 1% LB. After incubation for 3 hours at 37° C., organisms were diluted and spread on nutrient agar plates, incubated 1–2 days at 37° C., and colonies were counted.

Radial diffusion assay. The radial diffusion assay is a quantitative antimicrobial assay described by Lehrer and colleagues (Lehrer, R I, et al, 1991, "Ultrasensitive assays for endogenous antimicrobial polypeptides", *J Immunol Methods,* 137: 167–173). It can be used with a number of organisms; we used *Listeria monocytogenes* because Lehrer and colleagues found it to be very sensitive to antimicrobial peptides in this assay. This assay has the advantage of being simple and quantitative, but it is limited by being relatively labor intensive for large numbers of samples. *L. monocytogenes* were grown overnight in 3% (w/v) trypticase soy broth (TSB). Five ml of this culture was used to inoculate 50 ml of 3% TSB, and cells were grown for 3 hours at 37° C. Bacteria were centrifuged and resuspended in 5 ml of 10 mM potassium phosphate pH 7.4. Bacteria were diluted to give 4×106 cfu in 10 ml of warm (43° C.) 1% agarose (low electroendosmosis, Boehringer Mannheim) with 0.1% TSB and 10 mM potassium phosphate pH 7.4. Wells of 3 mm diameter were punched in the agarose, and 5 µl samples were placed in the wells and allowed to diffuse for 3 hours at 37° C. Plates were then overlaid with 1% agar containing 6% TSB. Following overnight incubation, the diameter of the clear zone was measured. Clearing activity was expressed in units, defined as the diameter of the clear zone minus the diameter of the central well (0.1 mm=1 U). For experiments with salt, the underlay agar contained the indicated amount of NaCl. For the pH experiments, the underlay agar contained a buffer mixture to cover the pH range of interest: 5 mM (each) ammonium acetate, MES, phosphoric acid, TAPS, adjusted to pH 5.0 to 9.0 with acetic acid or ammonium hydroxide. Some experiments included HNP-2 (Bachem) or protegrin-1 (IntraBiotics).

Luminescence assay. We developed a luminescence antimicrobial assay that is sensitive, quantitative, and able to handle large numbers of samples. This assay measures antimicrobial activity as a decrease in energy-dependent luminescence of *Escherichia coli* DH5α containing the luminescence plasmid pCGLS1 (Frackman, S, et al, 1990, "Cloning, organization, and expression of the bioluminescence genes of *Xenorhabdus luminescens* . . . , *J Bacteriol",* 172: 5767–5773). Because *E. coli* are sensitive to the antibacterial factor in ASF, the assay provided us with a quantitative test of antibacterial factor in the very small amounts of available ASF. *E. coli* DH5α containing pCGLS1 (Frackman, S, et al, 1990, "Cloning, organization, and expression of the bioluminescence genes of *Xenorhabdus luminescens* . . . , *J Bacteriol",* 172: 5767–5773) were grown to log phase at 30° C. and resuspended to $10^7$ bacteria/ml in 10 mM potassium phosphate pH 7.4 with 1% Luria-Bertani medium. Bacteria ($10^6$) were incubated with antimicrobial samples or column fractions in 96-well plates (Optiplate, Packard Instruments) in a total volume of 150 µl. After incubation at 30° C. for 4 hours, luminescence was measured with a luminometer (Anthos Labtech). Units of activity were determined. Briefly, samples were serially diluted in 96-well plates and tested for their ability to decrease luminescence. One unit is the amount of sample required to decrease luminescence by 50%.

Properties of antibacterial factor in ASF.

Gel filtration. Samples in 200 μl were loaded on a 20 cm×1 cm column of Sephadex G25 equilibrated in 100 mM ammonium acetate, pH 8.5. The column was run at 0.5 ml/min, and fractions of 0.5 ml were collected. Fractions were lyophilized overnight, resuspended in 100 μl $H_2O$, and assayed using the radial diffusion and luminescence assays.

Anion and cation exchange. The cation exchange resin S Sepharose, and the anion exchange resin Q Sepharose (Sigma) were equilibrated in (pH5) 20 mM HEPES or 20 mM Tris buffer (pH9), respectively, titrated to pH 5 to 9 with NaOH or Hcl. ASF (100 μl) was incubated with 50 μl resin for 45 minutes at 4° C. Resin was removed by centrifugation, and the supernatant fluid was collected and tested for antimicrobial activity.

Reverse phase-HPLC (RP-HPLC). ASF was passed through a 10,000 Da cut-off filter (Centricon), lyophilized, and resuspended in water. The sample was acidified with an equal volume of 0.1% trifluoroacetic acid (TFA) in water. Sample was analyzed by RP-HPLC using an ALTEX Ultrasphere ODS C18 column. Fractions of 1 ml were eluted at 0.5 ml/min with a gradient of 0% acetonitrile for 30 minutes, 0–20% acetonitrile for 40 minutes, 20–100% acetonitrile for 40 minutes, 100% acetonitrile for 5 minutes. Absorbance was monitored at 200 nm and 280 nm. Fractions were lyophilized, resuspended in water, and assayed for activity.

Acid-urea gels. Samples were analyzed on acid-urea polyacrylamide gels as described by Lehrer and colleagues (Lehrer, R I, et al, 1991, "Ultrasensitive assays for endogenous antimicrobial polypeptides", *J Immunol Methods*, 137: 167–173). Gels were stained with 0.1% Coomassie in 25% methanol and 14% formaldehyde solution, and destained with 40% methanol and 1.5% formaldehyde solution.

Expression of known antimicrobial peptides in human airway epithelia.

Recent studies have shown that transcripts for hβD-1 are present in airway epithelia (Zhao, C, et al, 1996, "Widespread expression of β-defensin hβD-1 in human secretory glands and epithelial cells", *FEBS Lett.* 396: 319–322; McCray, P. B., et al, 1997, "Human airway epithelia express a β-defensin", *Am J Respir Cell Mol Biol*, 16: 343–349). To learn whether transcripts for other known antimicrobial peptides are present in human airway epithelia we used RT-PCR; as positive controls we used human neutrophils and T-84 epithelia. HNP-1 transcripts were detected in airway epithelia, consistent with the report that HNP-1 was present in human fetal and adult lung tissue (Bateman, A, et al, 1991, "The isolation and identification of multiple forms of the neutrophil granule peptides from human leukemic cells", *J Biol. Chem.*, 266: 7524–7530). We also amplified HNP-4, HD-5, and HD-6. Using degenerate cathelin-specific primers to identify members of that family, we amplified a single band from airway epithelia. The PCR products from airway epithelia were isolated, cloned, and sequenced. The coding sequences were identical to published sequences for the neutrophil defensins HNP-1, the intestinal defensins HD-5 and HD-6, and the cathelin CAP-18. One difference was found between the epithelial and neutrophil HNP-4 sequence: the epithelial sequence had an A whereas the neutrophil sequence had a G two bases downstream of the stop codon. The significance of this difference is unknown. These results indicate that airway epithelia contain mRNA for several known antimicrobial peptides.

We used Northern blots to compare levels of these mRNAs in airway epithelia to those in tissues where the peptides may be functionally important. Transcripts for several mammalian antimicrobial peptides are present in tissues at levels detectable by Northern blots (Jones, D. E., et al, 1992, "Paneth cells of the human small intestine express an antimicrobial peptide gene", *J. Biol. Chem.*, 267: 23216–23225; Jones, D. E. et al., 1993, "Defensin-6 mRNA in human Paneth cells: implications for antimicrobial peptides in host defense of the human bowel", *FEBS Lett.*, 315: 187–192; Diamond, G, et al, 1993, "Airway epithelial cells are the site of expression of a mammalian antimicrobial peptide gene", *Proc Natl Acad Sci USA*, 90: 4596–4600. mRNA for HNP-1/HNP-3 and HNP-4 were present in neutrophils HD5 and HD6 were detected in small intestine. T84 RNA and CAP-18 was detected in testis. In contrast, none of these transcripts were detected in airway epithelia, even though the same or more airway epithelial RNA was analyzed. Moreover, these RNAs were not detected even with longer exposures or with a radioactivity imager. The data show that transcripts encoding these known antibacterial peptides are present at very low levels in human airway epithelia. Thus they are similar to reports that hβD-1 is present at low levels in airway epithelia (Zhao, C, et al, 1996, "Widespread expression of β-defensin hβD-1 in human secretory glands and epithelial cells", *FEBS Lett.* 396: 319–322; McCray, P. B., et al, 1997, "Human airway epithelia express a b-defensin", *Am J Respir Cell Mol Biol*, 16: (In Press)).

Stability of the antibacterial activity in ASF.

Evaluation of the antibacterial activity in ASF requires some knowledge of its stability. We found that ASF which had been heated to 100° C. for 10 minutes retained 75% of the initial activity. Moreover the following enzyme treatments had no effect on the antibacterial activity in ASF: treatment of 50 units of activity with trypsin, chymotrypsin, or proteinase K (1 μg/ml for 90 minutes at 30° C.), treatment of 4.5 or 45 units of activity with 3 units of Type II, VI, or XIII lipase, or treatment with 1 μg/ml bovine DNase for 2 hours at 30° C. These data suggest that the factor is reasonably stable and resistant to a number of enzymes. These properties are similar to a number of known antibacterial peptides.

Effect of salt on antibacterial activity in ASF.

Figure 22:
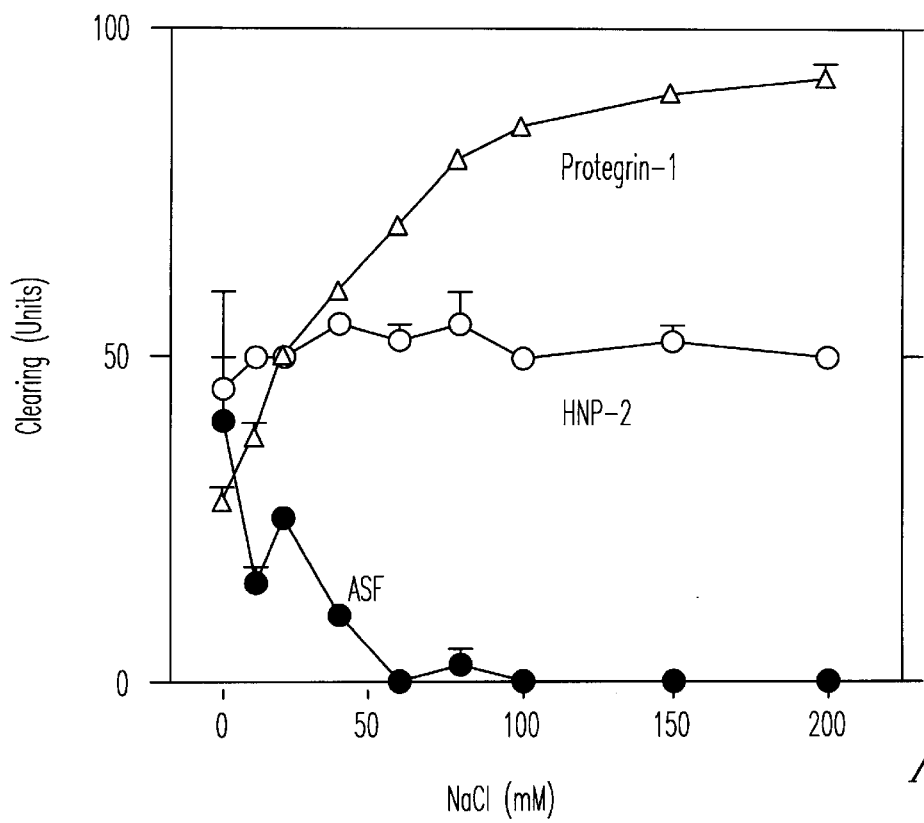
FIG. 22 is a graph depicting the time course of antibacterial factor production and effects of extracellular stimuli. A. Time course. ASF was collected from epithelia on several days and activity was assayed with the luminescence assay. Data represent average ±SEM of triplicate determinations.

We previously showed that the antibacterial factor in ASF is inhibited by high salt concentrations in a *P. aeruginosa* plating assay (Smith, J. J., et al, 1996, "Cystic fibrosis airway epithelia fail to kill bacteria because of abnormal ASF", *Cell*, 85: 229–236) and in the *E. coli* luminescence assay (Conway). FIG. 22 shows that ASF also had the greatest activity against *L. monocytogenes* at low concentrations of NaCl. In contrast, FIG. 22 shows that the activity of HNP-2 was insensitive to salt (also Porter and Ganz, personal communication) and the activity of protegrin-1 was stimulated by salt (see also Harwig, SSL, et al, 1996, "Intramolecular disulfide bonds enhance the antimicrobial and lytic activities of protegrins at physiological sodium chloride concentrations", *Eur. J. Biochem.* 240: 352–357). These data show that high salt concentrations inhibit activity of the ASF antibacterial factor toward several different bacteria. They also show that multiple different assays can detect the antibacterial activity in ASF. Finally, they suggest that a salt-insensitive antibacterial factor might be of value in CF airway epithelia.

Effect of pH on antibacterial activity in ASF.

Figure 23:
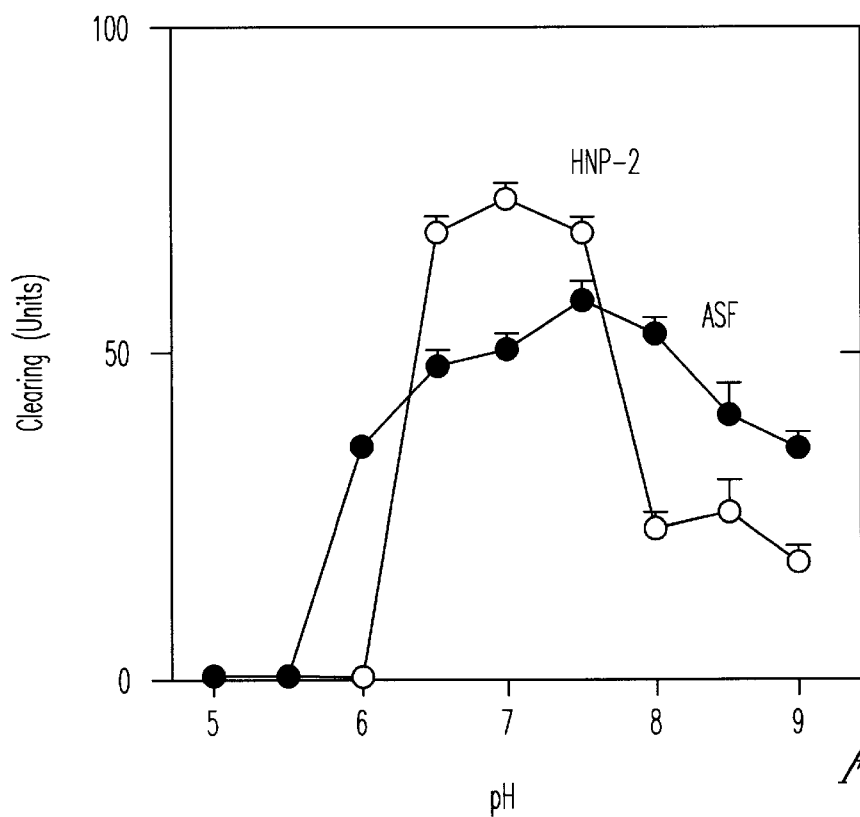
FIG. 23 is a graph depicting the effects of pH (left panel) and NaCl (right panel) on bactericidal activity of ASF. Activity was measured with the Listeria radial diffusion assay. The underlay agar was adjusted to the indicated pH or salt concentration as described in "Materials and Methods." Five microliters containing either ASF (ten-fold concentrated), 2 μg of HNP-2 or 2 μg of protegrin-1, were applied to the wells. Data indicate the average±range of duplicate determinations.

We examined the pH-dependence of the antibacterial factor in ASF and compared it to that of HNP-2. We used the agar diffusion assay because that assay is relatively insensitive to changes in pH (Lehrer, R I, et al, 1991, "Ultrasensitive assays for endogenous antimicrobial polypeptides", *J Immunol Methods,* 137: 167–173). FIG. 23 shows that ASF had the greatest activity near neutral pH. HNP-2 showed a similar pH-dependence, as previously reported. Decreased activity at high and low pH was not due to destruction of the factor; when we exposed ASF (50 units) to extremes of pH (trifluoroacetic acid, pH, 1.7 or Na$^+$ hydroxide, pH 12 for 150 minutes at 30° C.) and then measured activity at pH 7 with the luminescence assay, activity was not reduced.

Figure 24:
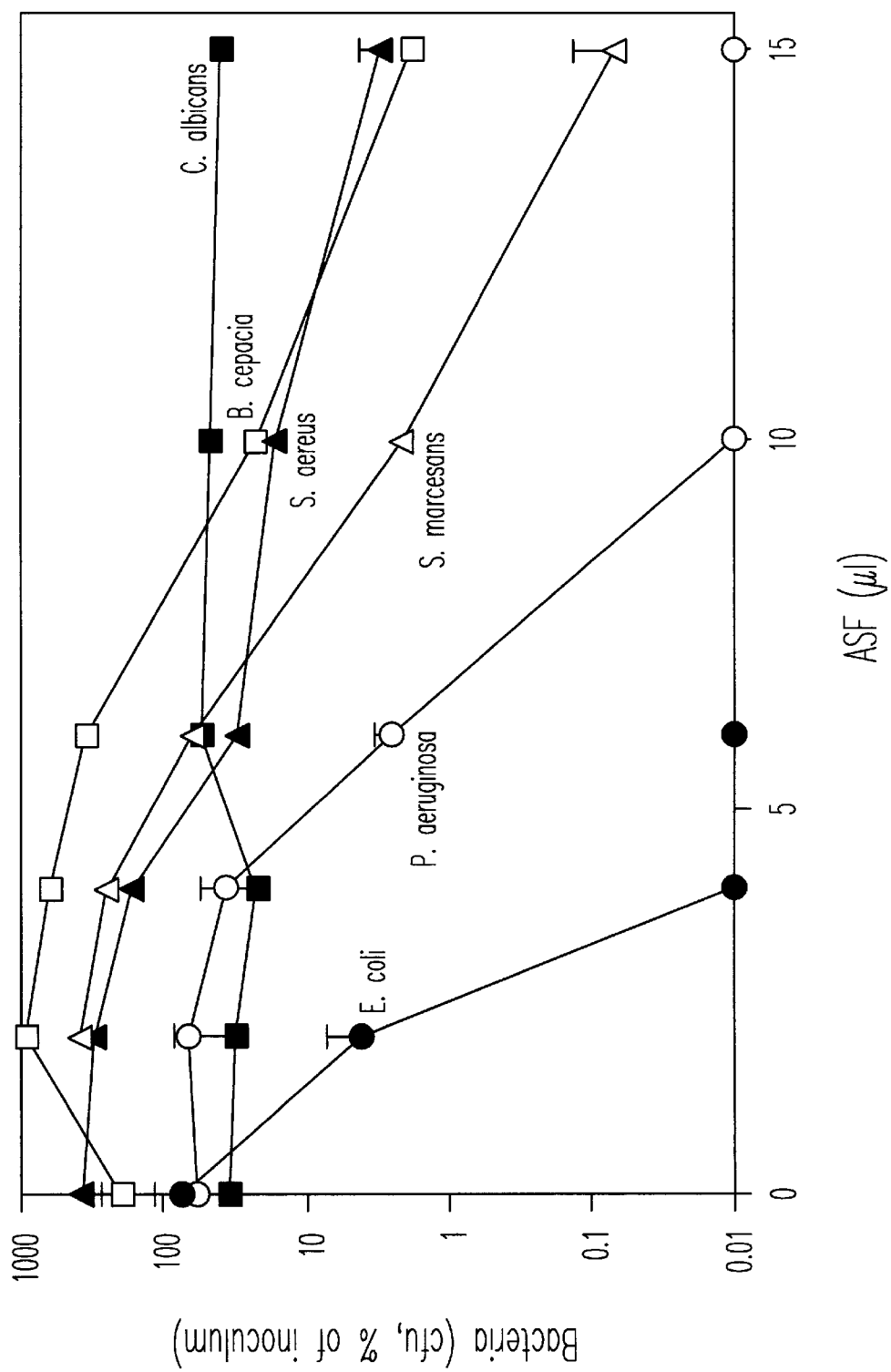
FIG. 24 is a graph depicting the antibacterial activity of ASF against several microbes. Organisms were incubated with the indicated amount of ASF in 1% LB for 3 hours at 37° C., then surviving organisms were plated and counted.

Antimicrobial spectrum of ASF.

Where they have been tested, most known antibacterial peptides are effective against a variety of microorganisms. To test the antimicrobial spectrum of ASF, we incubated several bacterial strains with varying doses of ASF (FIG. 24). ASF manifested broad spectrum bactericidal activity. The data show the following rank-order of potency: *E. coli*>*P. aeruginosa*>*S. marcesans*>*B. cepacia*>*S. aureus*. *S. pneumoniae* and the yeast *C. albicans* were not killed by ASF. These results show that the factor can kill both gram-positive and gram-negative bacteria, and confirm that the factor is bactericidal, not bacteriostatic.

Size of the antibacterial factor.

Figure 25:
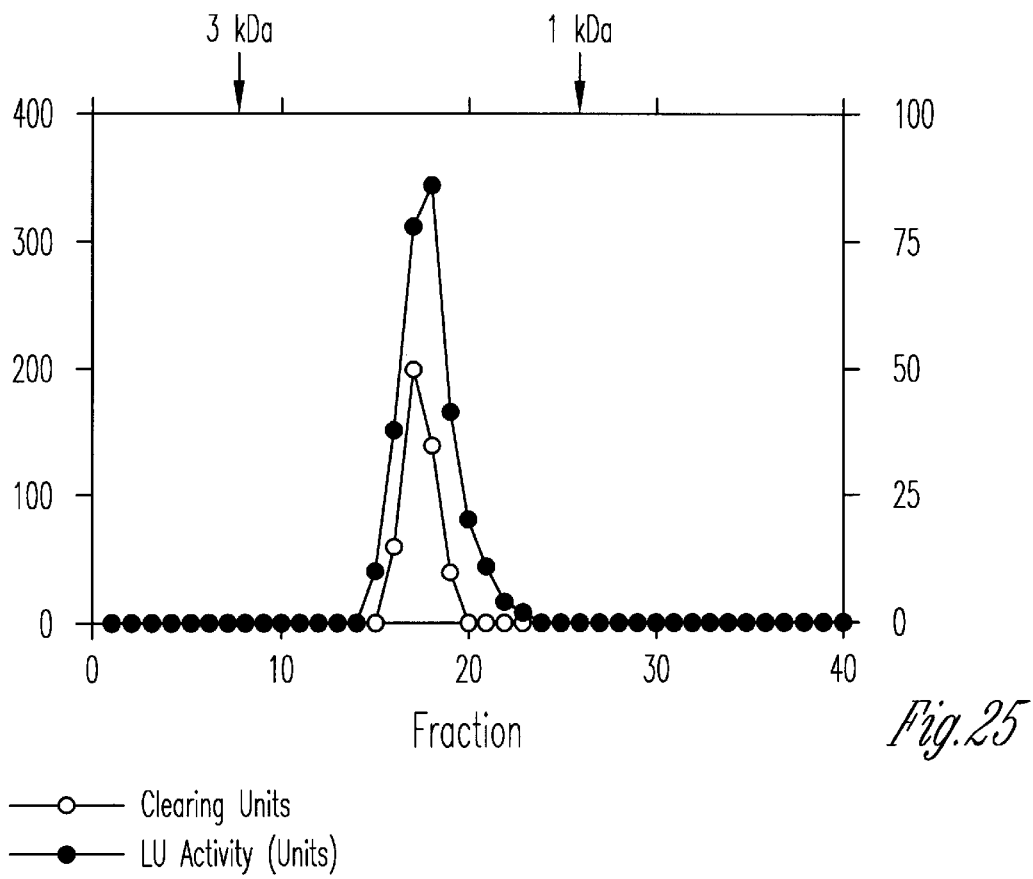
FIG. 25 is a graph depicting the gel filtration of ASF antibacterial factor. ASF was analyzed by gel filtration. Fractions were collected, lyophilized, and assayed for antibacterial activity in the luminescence assay and the radial diffusion assay.

We found that more than 90% of the ASF activity passed through a 10,000 molecular weight cut-off dialysis membrane (not shown). FIG. 25 shows that the factor migrated as a single peak between 1–3 kDa on a G25 gel filtration column. Recovery of activity from the column was 94%, so the peak represents the majority of the activity. These data indicate that the factor is small, as are most known antimicrobial peptides.

Charge of the antibacterial factor.

Figure 26:
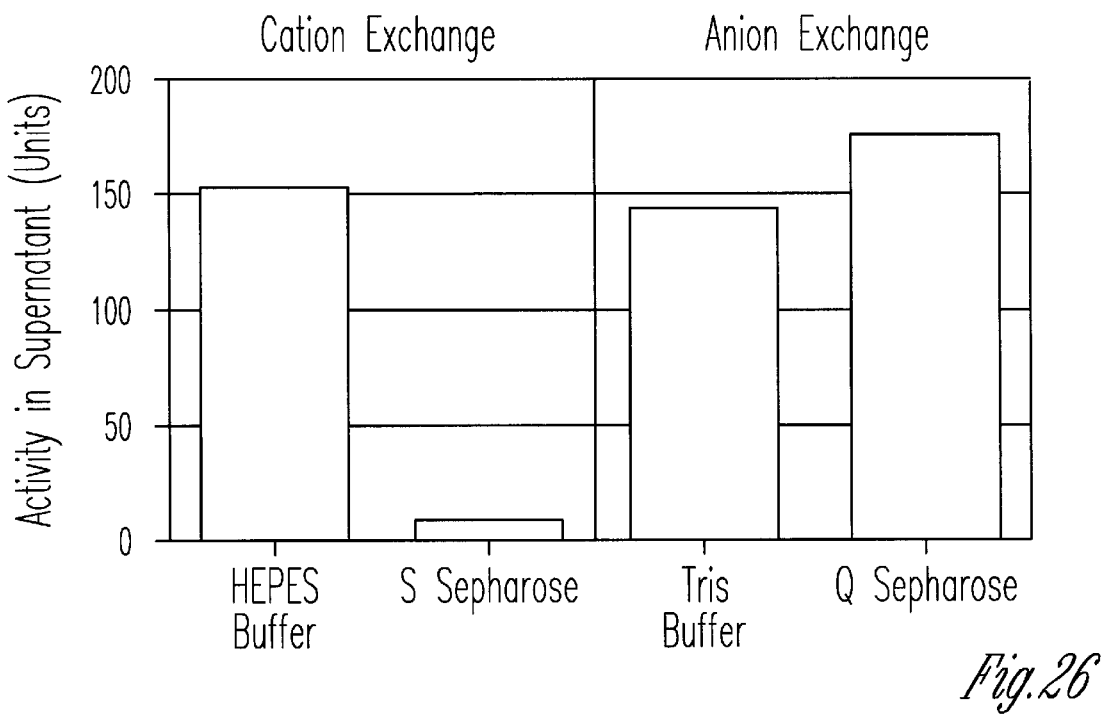
FIG. 26 is a graph depicting the ion exchange chromatography of ASF. ASF was incubated with the indicated ion exchange resin, and the supernatant was assayed for antibacterial activity using the luminescence assay. in the luminescence assay.

Most known antimicrobial peptides are cationic molecules, although anionic antibacterial peptides have been discovered in ovine bronchoalveolar lavage fluid. To test the ASF factor, we asked whether it bound to an anionic or cationic exchange resin. FIG. 26 shows that the factor was depleted from solution by a cation exchange resin, but not by an anion exchange resin. We obtained similar results over the pH range of 5.0 to 9.0. This result suggested that the airway antibacterial factor is cationic, like most known antibacterial peptides.

Relative potency of the antibacterial factor in ASF.

Figure 27A:
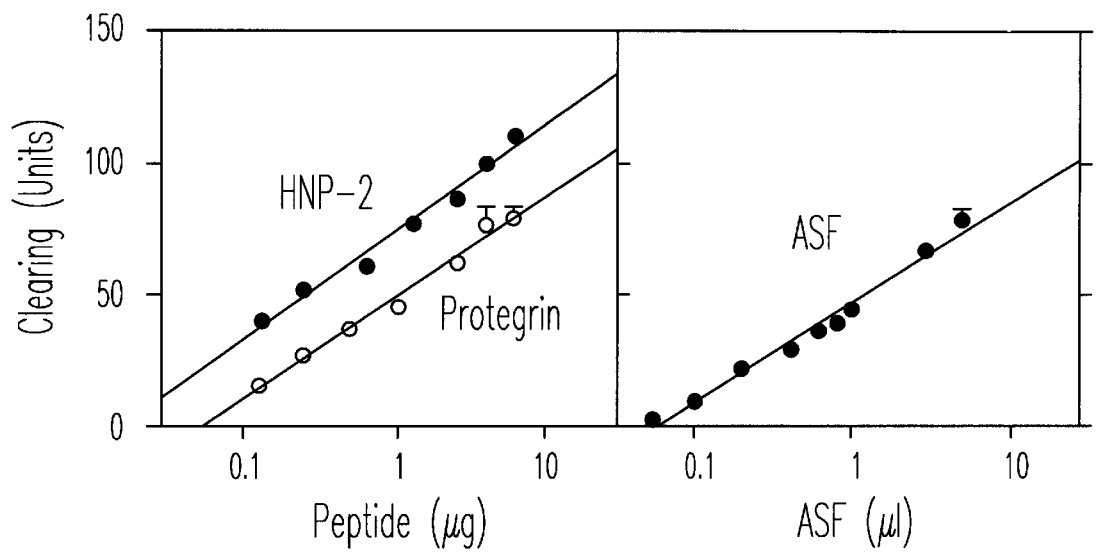
FIGS. 27(A–B) are graphs depicting the dose-response of ASF, HNP-2, and protegrin-1 in the Radial Diffusion and Luminescence Assays. Peptides and fluid were diluted in 0.1% bovine serum albumin, and assayed as described in Material and Methods.
Figure 27B:
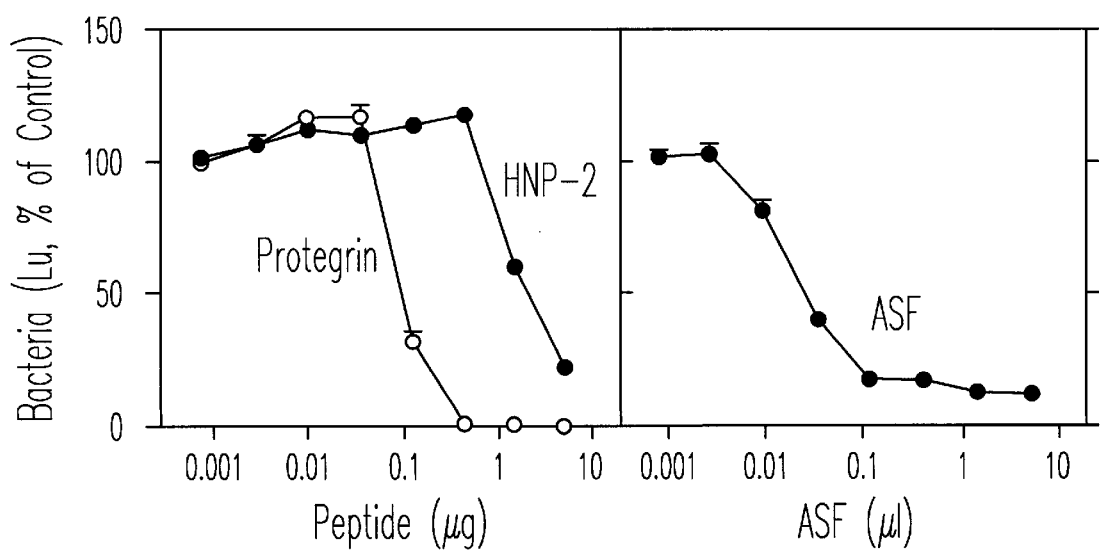

Although we do not know how much factor is present in ASF, it may be useful to compare its relative potency to that of known antibacterial peptides. FIGS. 27(A–B) compare the antibacterial potency of ASF with that of HNP-2 and PG-1 using the radial diffusion assay. For these experiments, we used ASF concentrated 10-fold by lyophilization to obtain a large clearing zone in the radial diffusion assay. All three samples showed good clearing activity: 1 µl of concentrated ASF had activity equivalent to 0.23 µg HNP-2 or 0.9 µg PG-1. FIG. 26B shows a comparison using the *R. voli* luminescence assay. In this assay, 1 Unit of concentrated ASF (73 nl) decreased luminescence to the same extent as 0.1 µg of PG-1 or 2.1 µg of HNP-2. These data demonstrate that relative antibacterial potency is dependent on the test organism and the assay: HNP-2 was more potent than PG-1 in the *L. monocytogenes* radial diffusion assay, whereas PG-1 was more potent than HNP-2 in the *E. coli* luminescence assay. Although these assays cannot be used to estimate how much factor is in ASF, it appeared that µl volumes of ASF contained as much antibacterial activity as µg amounts of HNP-2 and PG1.

Based on these results, we asked whether there was a peptide present in ASF that resembled known antibacterial peptides. If such a peptide had a potency in the same range as that of HNP-2 or protegrin, we might expect to see it on peptide gels to which we applied 100 units of ASF antibacterial activity. We used several types of gels including acid-urea polyacrylamide gels, because Lehrer and colleagues (Lehrer, R I, et al, 1991, "Ultrasensitive assays for endogenous antimicrobial polypeptides", *J Immunol Methods,* 137: 167–173) have shown them to be helpful in analysis of cationic antibacterial peptides. ASF which had been passed through a 10 kDa-cutoff filter to remove large proteins showed no protein bands. Staining of HNP2 was used as a control. These results suggest that if the activity of ASF is due to a peptide, it may be different from known antibacterial peptides or it may have unique properties that allow it to be washed out of the formaldehyde-fixed gel.

Behavior of the antibacterial factor on RP-HPLC.

All previously identified antibacterial peptides have some hydrophobic properties and thus bind to RP-HPLC columns (Ganz, T, et al, 1985, "Defensins: natural peptide antibiotics of human neutrophils", *J Clin Invest,* 76: 1427–1435; Wilde, C G, et al, 1989, "Purification and characterization of human neutrophil peptide 4, a novel member of the defensin family", *J Biol Chem,* 264: 11200–11203; Bensch, K W, et al, 1995, "hBD-1: a novel b-defensin from human plasma", *FEBS Lett,* 368: 331–335; Kokryakov, V N, et al, 1993, "Protegrins: leukocyte antimicrobial peptides that combine features of corticostatic defensins and tachyplesins", *FEBS Lett,* 327: 231–236). Therefore, we examined the behavior of ASF on a C18 RP column. ASF antibacterial activity eluted in the 0% acetonitrile flow-through of an C18 column (ALTEX Ultrasphere). Activity also passed through three other types of RP-HPLC columns (Vydac C18, Hamilton PRP1, and Hamilton PRP3), as well as through Bond Elut C18 cartridges (Varian). These data indicate that the antibacterial factor is hydrophilic.

A single peak of activity was resolved with 195% recovery of activity. We often observed greater than 100% recovery of activity from the RP columns; this may be due to removal of inhibitory factors present in ASF. This suggests that the factor may interact with binding proteins that somehow modulate its activity. Knowledge of such factors might provide new strategies for therapeutics.

The low affinity for RP columns places the behavior of the ASF antibacterial factor in sharp contrast to that of known human antibacterial peptides on similar columns; such peptides usually require greater than 20% acetonitrile for elution (Ganz, T, et al, 1985, "Defensins: natural peptide antibiotics of human neutrophils", *J Clin Invest,* 76: 1427–1435; Wilde, C G, et al, 1989, "Purification and characterization of human neutrophil peptide 4, a novel member of the defensin family", *J Biol Chem,* 264: 11200–11203; Bensch, K W, et al, 1995, "hBD-1: a novel β-defensin from human plasma", *FEBS Lett,* 368: 331–335; Kokryakov, V N, et al, 1993, "Protegrins: leukocyte antimicrobial peptides that combine features of corticostatic defensins and tachyplesins", *FEBS Lett,* 327: 231–236). Because of previous reports that hBD-1 transcripts are present in human airway epithelia (Zhao, C, et al, 1996, "Widespread expression of beat-defensin hBD-1 in human secretory glands and epithelial cells", *FEBS Lett.* 396: 319–322; McCray, P. B.,et al, 1997, "Human airway epithelia express a β-defensin", *Am J Respir Cell Mol Biol,* 16: (In Press)), we tested the hypothesis that hBD-1 migrates at the same location as the antibacterial activity in ASF. We found that as previously reported hBD-1 was hydrophobic, eluting from the C18 column in about 30% acetonitrile.

On one hand, our data show that the antibacterial factor in ASF has several properties that are similar to known antibacterial peptides from humans and other species. It is relatively stable and resistant to heat and several enzymes. It is salt-sensitive, and most active at neutral pH (Odeberg, H et al, 1975, "Antibacterial activity of cationic proteins from human granulocytes", *J Clin Invest,* 56: 1118–1124; Selsted, M E, et al, 1984, "Purification and antibacterial activity of antimicrobial peptides of rabbit granulocytes", *Infect. Immun.,* 45: 150–154; Lehrer, R I, et al, 1983, "Antibacterial activity of microbicidal cationic proteins 1 and 2, Natural peptide antibiotics of rabbit lung macrophages", *Infect. Immun.,* 42: 10–14; Skerlavaj, B, et al, 1990, "Rapid membrane permeabilization and inhibition of vital functions of gram-negative bacteria by bactenecins", *Infect. Immun.* 58: 3724–3730). Like several known antibacterial peptides, the ASF antibacterial factor is bactericidal, not bacteriostatic, and killed both gram negative and gram positive bacteria.

On the other hand, the data allow us to distinguish the ASF antibacterial factor from known peptides. First, it is small, a feature indicating it is not one of the known antibacterial proteins from submucosal glands: lysozyme, lactoferrin, or secretory leukocyte proteinase inhibitor. Second, it is cationic, a property that distinguishes it from the anionic bactericidal peptides of ovine surfactant Brodgen, K A, et al, 1996, "Isolation of an ovine pulmonary surfactant-associated anionic peptide bacterial for *Pasteurella haemolytica*", Proc. Natl Acad Sci USA, 93: 412–416). Third, it is salt-sensitive, whereas the HNP-2 and porcine protegrins are salt-resistant. Fourth, the lack of activity against *C. albicans* distinguishes it from the α-defensins of neutrophils (Wilde, C G, et al, 1989, "Purification and characterization of human neutrophil peptide 4, a novel member of the defensin family", *J Biol Chem,* 264: 11200–11203), bovine β-defensin TAP (Diamond, G., et al., 1991, "Tracheal antimicrobial peptide, a cysteine-rich peptide from mammalian tracheal mucosa: peptide isolation and cloning of a cDNA", *Proc. Natl. Acad. Sci. USA,* 88: 3952–3956), and porcine protegrins (Kokryakov, V N, et al, 1993, "Protegrins: leukocyte antimicrobial peptides that combine features of corticostatic defensins and tachyplesins", *FEBS Lett,* 327: 231–236).

However, the most telling property of the antibacterial factor in ASF is its low hydrophobicity. This characteristic indicates that the antibacterial factor in ASF is not hBD-1 nor is it another known antibacterial peptide. More importantly, this result suggests that the factor is a novel hydrophilic molecule.

Our results also have implications for defense of the normal airway and defects in CF. The decrease in activity at low pH values suggest that it will not be active at the low pH often observed in lung abscess. Presumably clearance of such late-stage infections relies on phagocytic cells and acquired immunity.

We found that the *E. coli* was very sensitive to the factor in ASF (even at high salt concentrations, Conway). This may be the reason that *E. coli* infections are rare in both normal and CF individuals. In contrast, the factor did not kill *S. pneumonia.* This result may explain the observation that *S. pneumonia* infections are relatively common in both normal people and people with CF, and yet are not more common in CF. Killing of *P. aeruginosa* showed an intermediate sensitivity to the factor and was salt-sensitive; this may explain in part the observation that *P. aeruginosa* commonly colonizes CF airways. It is interesting that *S. marcesans, B. cepacia,* and *S. aureus* also showed intermediate sensitivity and also are found in CF airway infections. However it is likely that other factors such as bacterial virulence, bacterial adherence, and antibiotic selection also contribute to the propensity for *P. aeruginosa* colonization and infection of the CF airway. In addition, the inability of the ASF factor to kill *S. pneumoniae* or *C. albicans* clearly indicate that other factors or mechanisms are also involved in defense of the airways.

ASF from differentiated, ciliated airway epithelia. This model has many similarities with intact tissue: the electrical properties are similar to those of native lung epithelia, and the epithelia have a mixture of ciliated and non-ciliated cells, like the in vivo airway. In addition, this culture system provides several distinct advantages. First, it allows us to analyze specifically the factors produced by epithelial cells. Second, the epithelia can be maintained in culture for several weeks, allowing repeated fluid collection. Third, the epithelia are covered with air; this may be important for function because fluid-covered and air-covered epithelia have different transcriptional activity. Fourth, this is the only model that has been demonstrated to manifest a CF defect in bacterial killing when bacteria are added directly to the epithelium. However, this system does not exactly reflect the properties of the airways in vivo. Other structures are present in airways, such as submucosal glands, which may produce additional factors and substances that may influence the production and/or activity of the factor produced by the epithelium. Moreover it is possible that material produced by the alveoli (such as surfactant lipids and proteins) might contribute to or affect antibacterial activity. However, in order to understand the system, we have focused on a simple model that involves only the airway epithelia without contribution from submucosal glands or alveoli, from macrophages, or from immune or inflammatory cells.

What is claimed is:

1. A method for killing infectious microbial cells in vivo or ex vivo comprising:
    exposing said infectious microbial cells to a treatment-effective amount of an antimicrobial factor which is isolated from human mucosal epithelial cells and having the following characteristics:
    (a) a molecular weight of less than 10 kd;
    (b) is stable at 100° C. for 10 minutes;
    (c) active against gram positive and gram negative bacteria;
    (d) active against fungi and methicillin resistant *Staphylococcus aureus;*
    (e) antimicrobial activity decreases with increasing salt concentration;
    (f) elutes as a peak that absorbs at 220 nm on a C18 reverse phase HPLC column between 8–9 minutes with solvent (0.1% trifluoroacetic acid, 60% acetonitrile, 30% isopropanol, 9.9% $H^2O$ molecules) eluted as a linear gradient from 0% to 60% solvent in 40 min, at a flow rate of 1 ml/min;
    (h) antimicrobial activity is unaffected by treatment with 50 units of activity of trypsin, chymotrypsin or proteinase K;
    (i) antimicrobial activity is unaffected with treatment with 3 units of activity of type II, VI, or XIII lypase;
    (j) antimicrobial activity is unaffected with treatment of 1 μg/ml bovine DNAse for 2 hours at 30° C.; and
    (k) is cationic.

2. The method according to claim 1 wherein the antimicrobial factor is administered in vivo at a dose of about 125 μg/kg of body weight.

3. A method of treating a mucosal infection in an animal in need of such treatment comprising:

administering to said animal an effective amount of an antimicrobial factor which is isolated from human mucosal epithelial cells and having the following characteristics:
(a) a molecular weight of less than 10 kd;
(b) heat stable;
(c) active against gram positive and gram negative bacteria;
(d) active against fungi and methicillin resistant *Staphylococcus aureus;*
(e) antimicrobial activity decreases with increasing salt concentration;
(f) elutes as a peak that absorbs at 220 nm on a reverse phase HPLC column between 8–9 minutes with solvent (0.1% trifluoroacetic acid, 60% acetonitrile, 30% isopropanol, 9.9% $H^2O$ molecules) eluted as a linear gradient from 0% to 60% solvent in 40 min, at a flow rate of 1 ml/min;
(h) antimicrobial activity is unaffected by treatment with 50 units of activity of trypsin, chymotrypsin or proteinase K;
(i) antimicrobial activity is unaffected with treatment with 3 units of activity of type II, VI, or XIII lypase;
(j) antimicrobial activity is unaffected with treatment of 1 μg/ml bovine DNAse for 2 hours at 30° C.; and
(k) is cationic.

* * * * *